(12) United States Patent
Hofeldt

(10) Patent No.: US 11,026,573 B1
(45) Date of Patent: Jun. 8, 2021

(54) MONOCULAR AND BINOCULAR RELATIVE FOCAL PHOTO-STRESS

(71) Applicant: Albert Hofeldt, Miami Beach, FL (US)

(72) Inventor: Albert Hofeldt, Miami Beach, FL (US)

( * ) Notice: Subject to any disclaimer, the term of this patent is extended or adjusted under 35 U.S.C. 154(b) by 114 days.

(21) Appl. No.: 16/371,070

(22) Filed: Mar. 31, 2019

Related U.S. Application Data

(60) Provisional application No. 62/656,350, filed on Apr. 11, 2018.

(51) Int. Cl.

| | |
|---|---|
| *A61B 3/08* | (2006.01) |
| *A61B 3/00* | (2006.01) |
| *A61B 3/14* | (2006.01) |
| *A61B 3/10* | (2006.01) |
| *A61H 5/00* | (2006.01) |
| *A61B 3/02* | (2006.01) |

(52) U.S. Cl.
CPC ............ *A61B 3/08* (2013.01); *A61B 3/022* (2013.01); *A61H 5/005* (2013.01)

(58) Field of Classification Search
CPC .. A61H 5/00; A61B 3/103; A61B 3/08; A61B 3/14; A61B 3/113; A61B 3/1208; A61B 3/1225; A61B 3/024; A61B 3/04; A61B 3/032; A61B 3/02; A61B 3/18; A61B 3/1015
USPC ........ 351/200–201, 203, 205–206, 209–211, 351/218, 221, 222, 239–240, 243–246
See application file for complete search history.

(56) References Cited

U.S. PATENT DOCUMENTS

| | | | |
|---|---|---|---|
| 5,080,478 A * | 1/1992 | O'Brien | A61B 3/063 351/224 |
| 7,290,878 B1 * | 11/2007 | Hofeldt | A61B 3/08 351/200 |
| 2013/0100400 A1 * | 4/2013 | Hofeldt | A61B 3/022 351/201 |

* cited by examiner

*Primary Examiner* — Dawayne Pinkney

(57) ABSTRACT

Photo-stress by focal light bleaches the retina and temporarily reduced retinal function. Recovery from suppression is measurable by monocular and binocular endpoints, when recovery is prolonged a disease is suspected. The monocular endpoint is the moment the dark central afterimage representing the macula becomes the same brightness as the peripheral ring representing unstimulated retina and the binocular endpoint is brightness equality of rivalrous stimuli. Four embodiments are described for measuring relative brightness sense photo-stress utilizing monocular and binocular methodology.

20 Claims, 23 Drawing Sheets

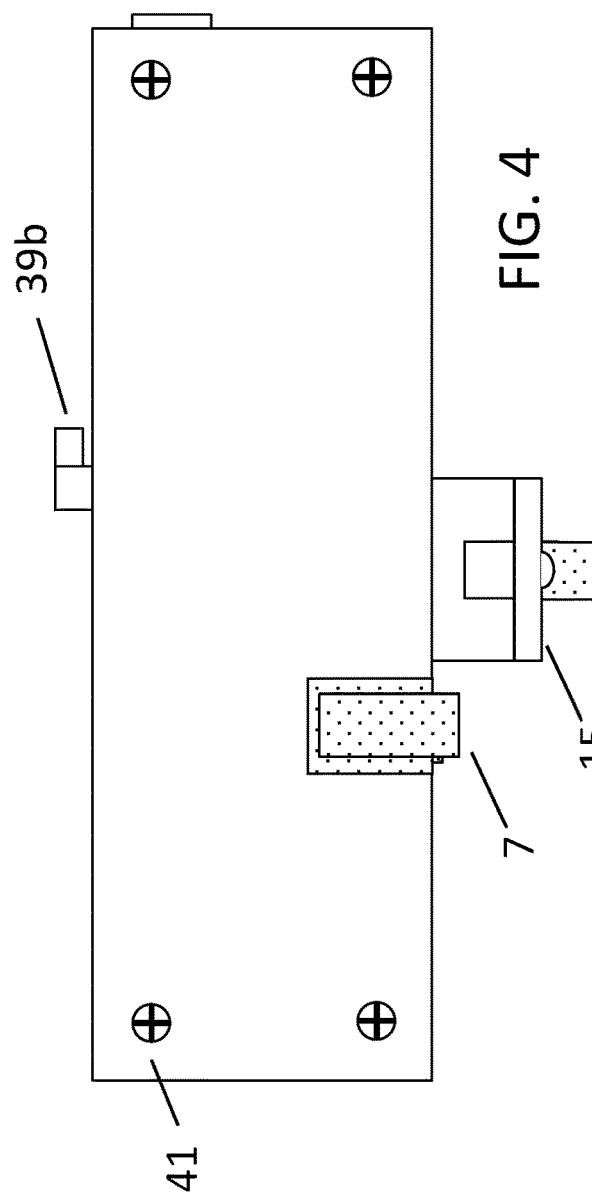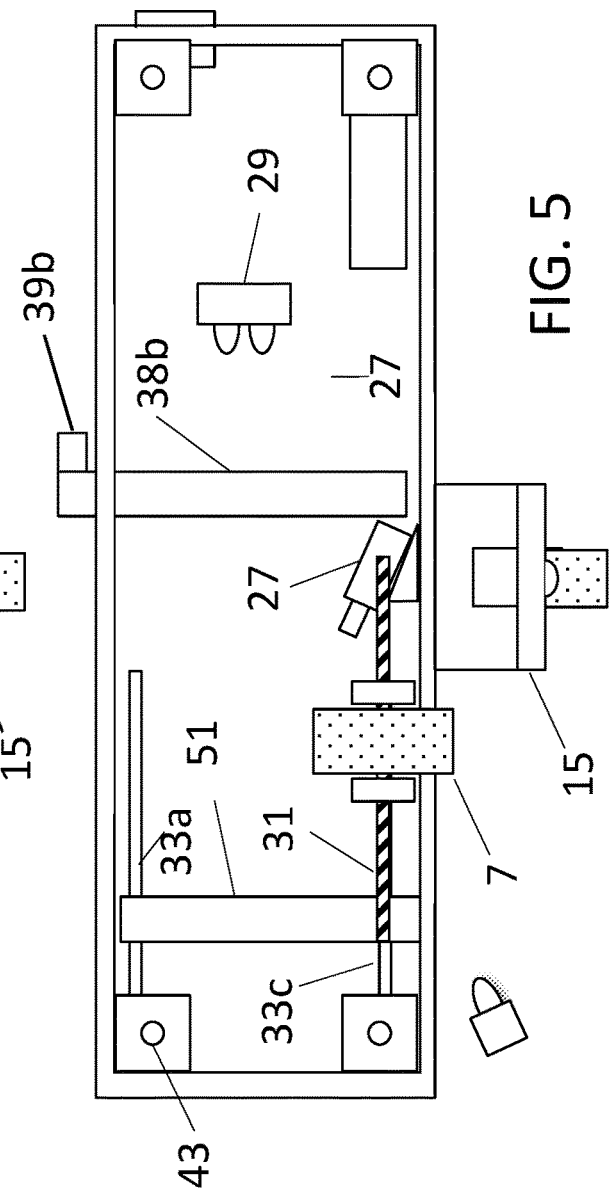

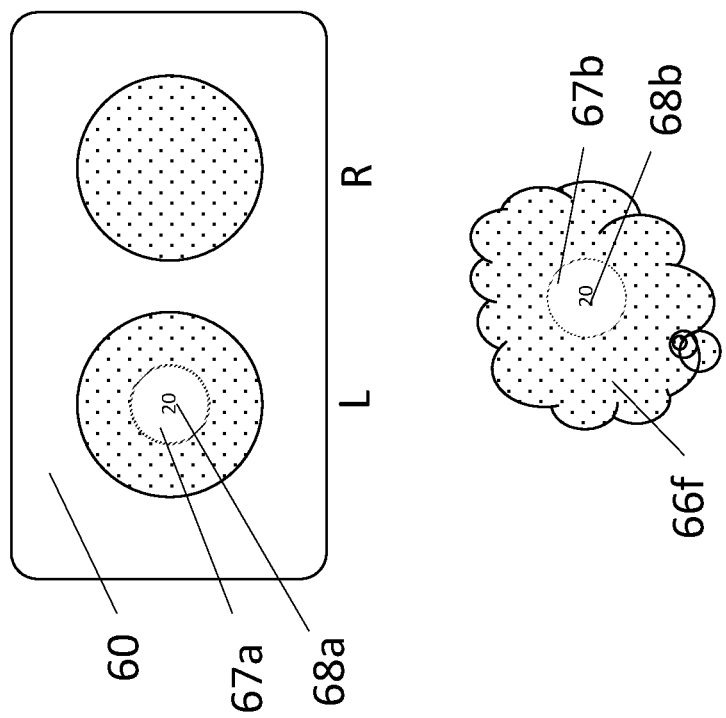
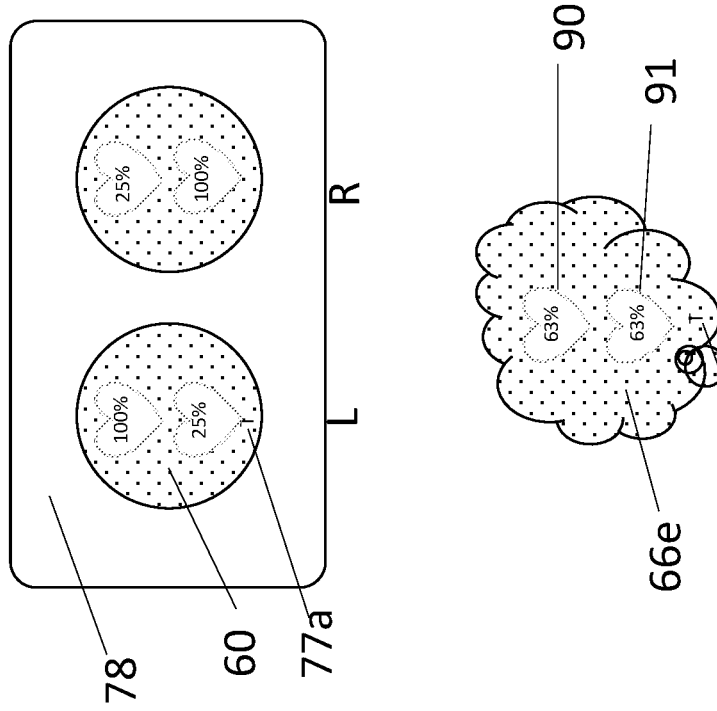

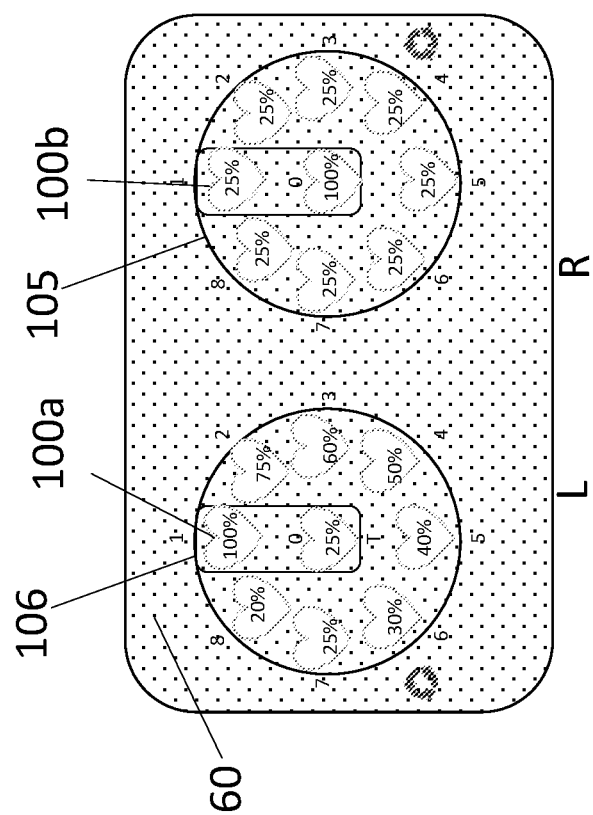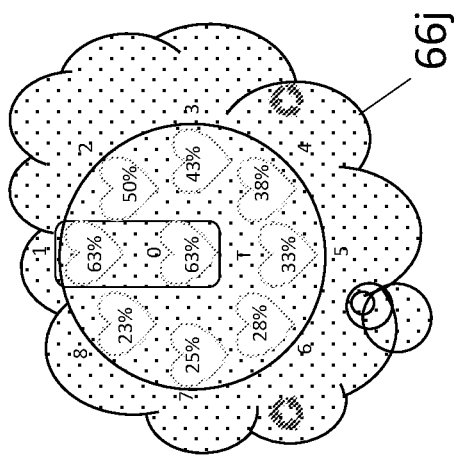
FIG. 25
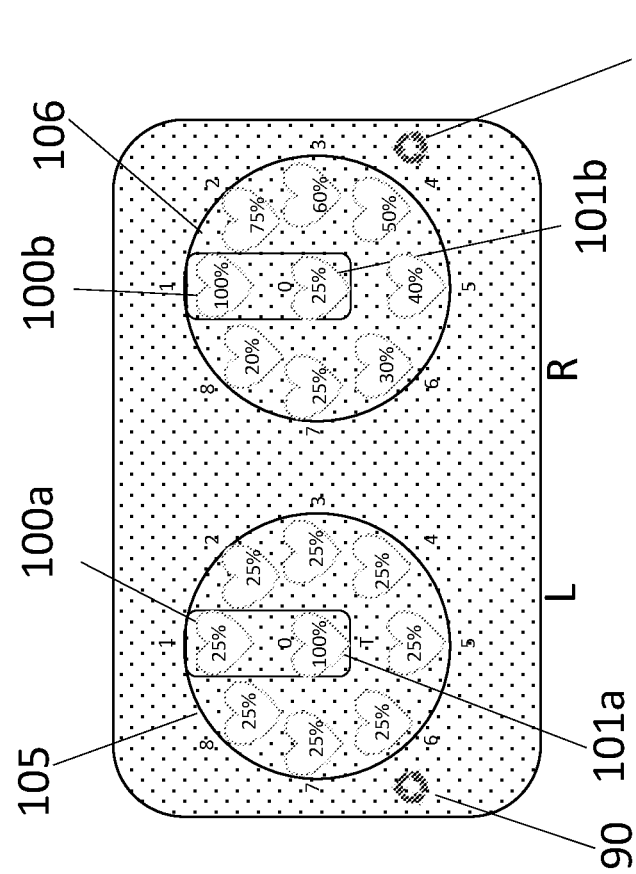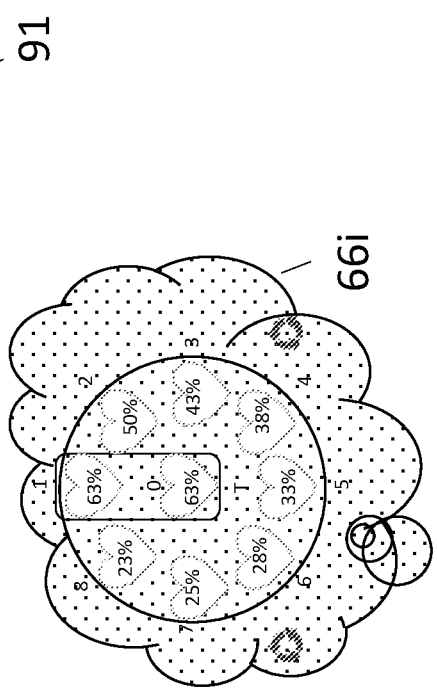
FIG. 24

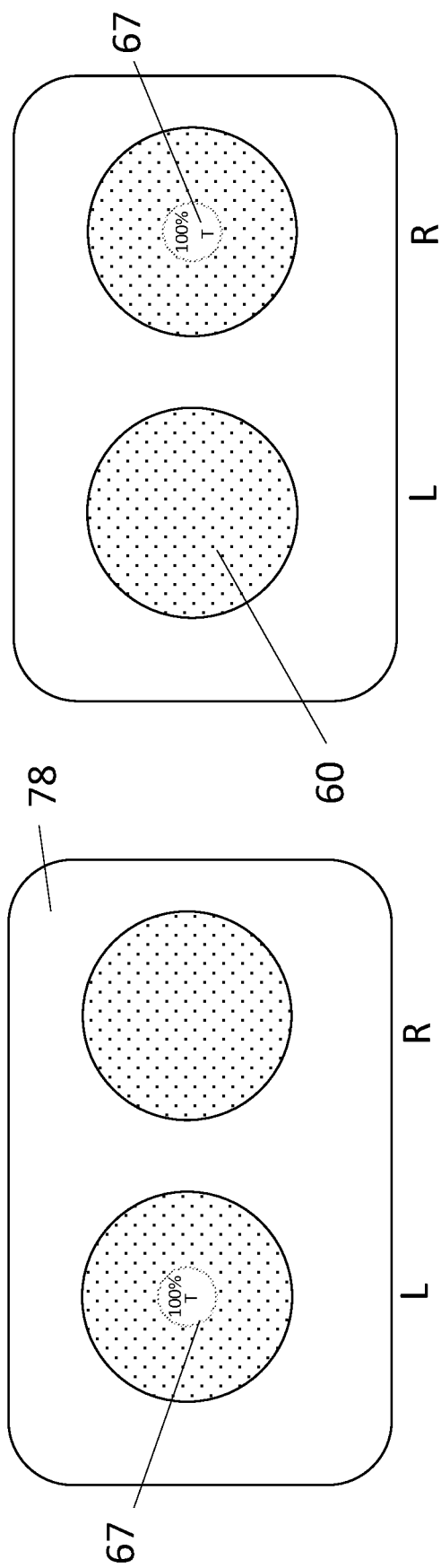
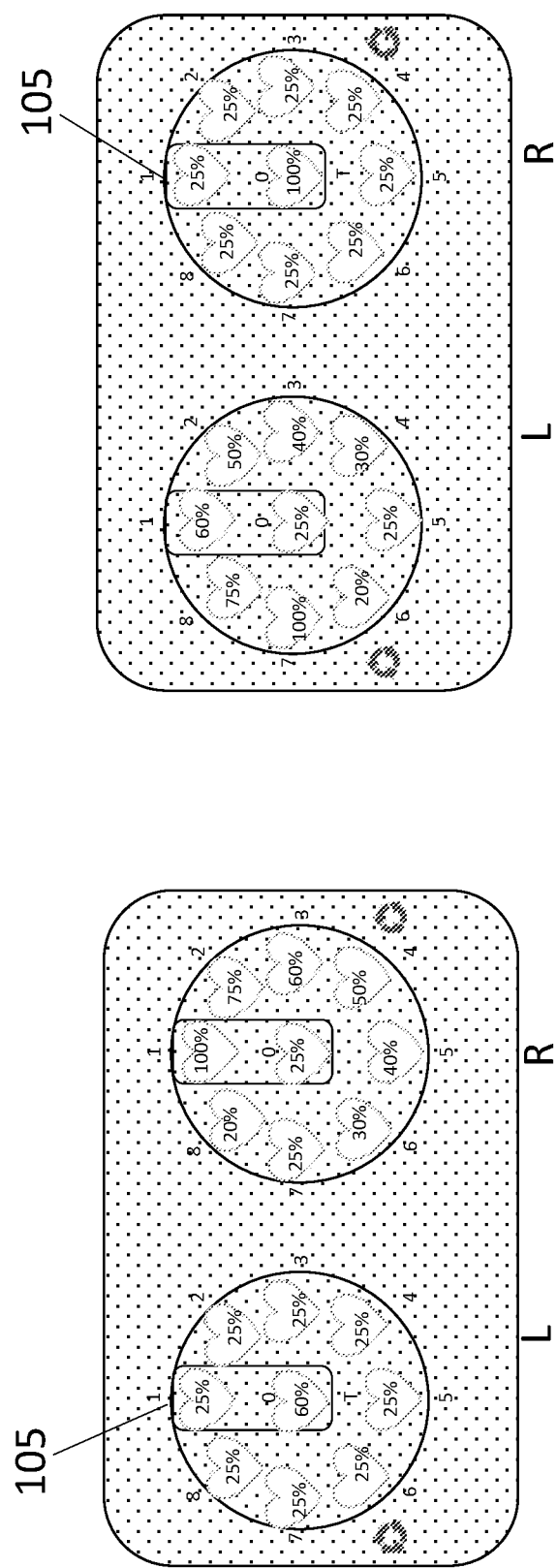
FIG. 26
FIG. 27

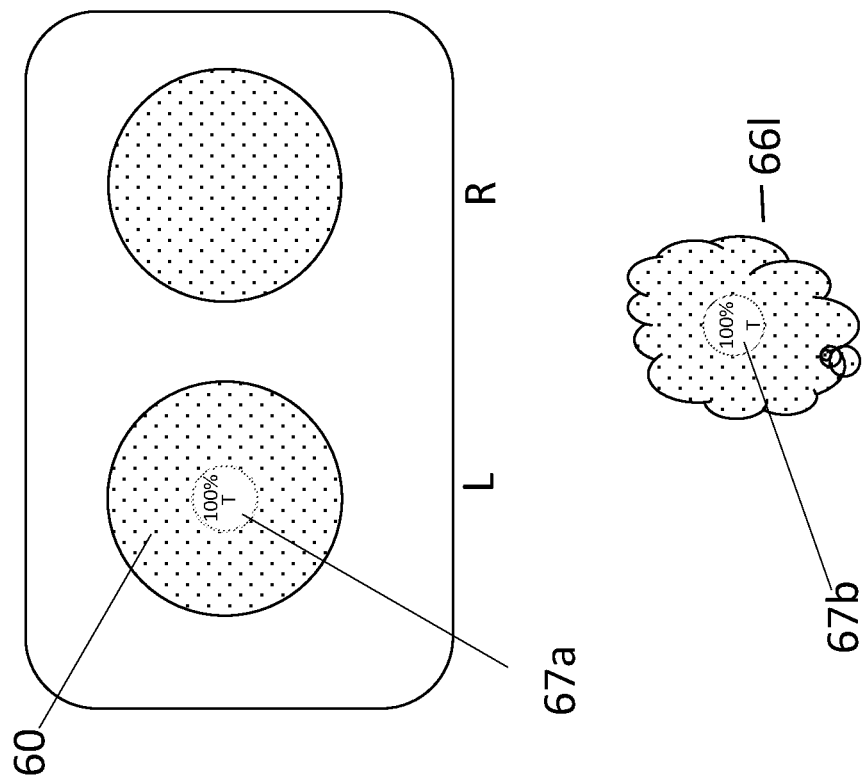
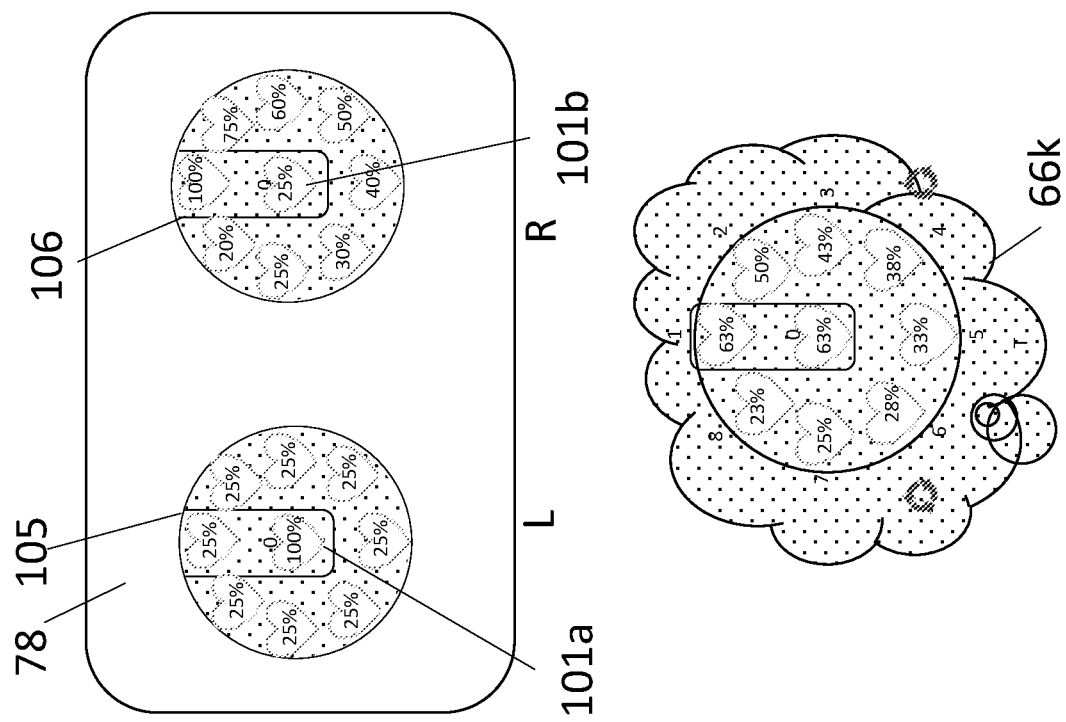
FIG. 29
FIG. 28

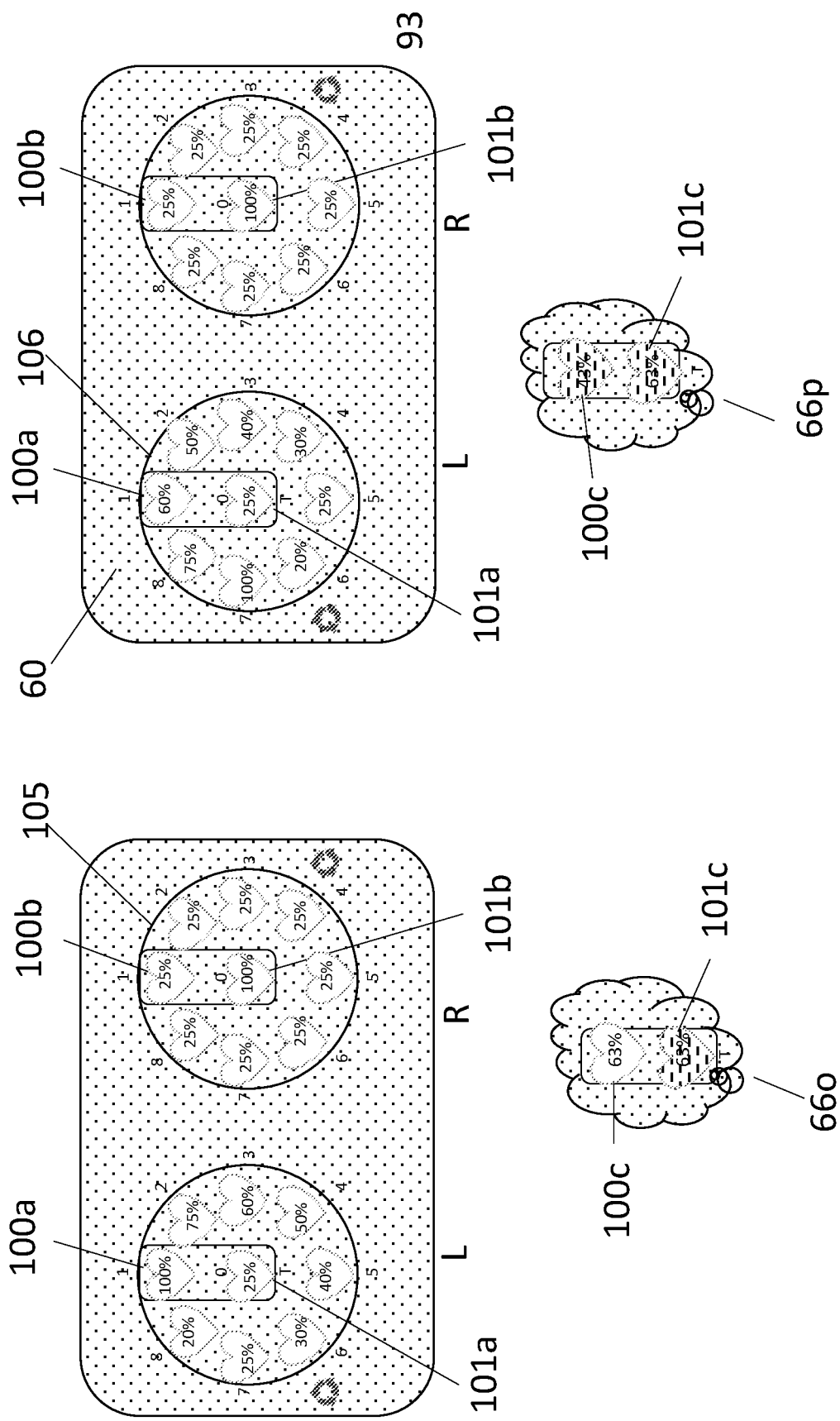

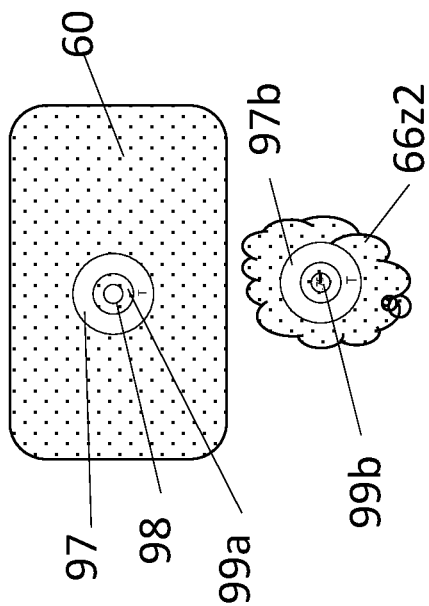
FIG. 40
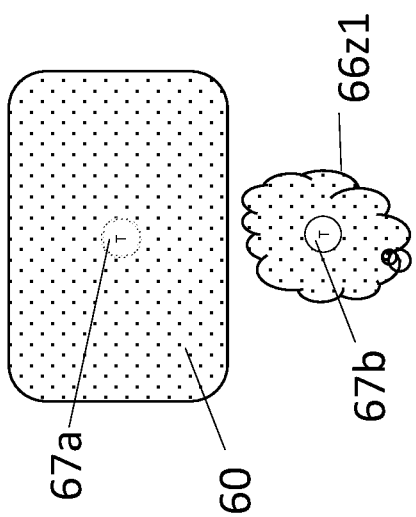
FIG. 41
FIG. 39

MONOCULAR AND BINOCULAR RELATIVE FOCAL PHOTO-STRESS

CROSS REFERENCE TO RELATED APPLICATIONS

Provisional patent application 62/656,350 dated Apr. 11, 2018

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATED-BY-REFERENCE OF MATERIAL SUBMITTED ON A COMPACT DISC OR AS A TEXT FILE VIA THE OFFICE ELECTRONIC FILING SYSTEM (EFS-WEB)

Not Applicable

STATEMENT REGARDING PRIOR DISCLOSURES BY THE INVENTOR OR A JOINT INVENTOR

Not Applicable

BACKGROUND OF THE INVENTION

Field of the Invention

This invention relates to monocular and binocular vision testing. To be more specific, this invention pertains to stressing the eye with light and measuring the time for vision function to return.

Related Art

U.S. Pat. No. 9,560,960, Patent Date Feb. 7, 2017. AMBLYOMETER FOR BALANCING BRIDGE RIVALROUS BINOCULAR VISION.

BRIEF SUMMARY OF THE INVENTION

Bleaching photoreceptors with light temporally suppresses visual function and is the basis for photo stressing the macula. Once bright light stimulation ceases, the recovery phase begins and the visual function begins to improve and eventually full vision returns. The time from cessation of stimulation and return of vision is termed the "recovery time" of the recovery period. Recovery time is prolonged in certain diseases of the macula, which provides important information for diagnosis and management.

The heretofore method of measuring the recovery time has been to stimulate one eye with a bright light, transfer sighting from the light source to a reading chart in a different location, and clock the recovery time, the ability to read letters or other symbols of a specified size. In my invention, recovery is measured by simultaneous comparison of relative stimulus brightness, in one embodiment the comparison is between the two eyes and in the other embodiment is between stressed and unstressed retina of the same eye. Photo-stress recovery time is measured first in one eye and then the other eye. The recovery time is usually 30 to 60 seconds for the normal eye. Depending upon the strength and duration of the stimulus, the normal recovery time can vary. In prior methods, the examiner uses whatever light source is handy; typically the indirect ophthalmoscope set-on bright, a penlight, or a fiber-optic curved examination light. The disadvantages of prior methods of photo-stress testing are: (1) lack of sensitivity because the difference between normal and abnormal recovery times are often very similar, particularly in mild disease states, (2) the brightness stimulus is often not standardized among investigator, (3) using the identification of symbols as the endpoint, the endpoint may not be solely dependent on recovery time since confounding visual problems, such as cataract that reduces visual acuity or patchy vision in macular degeneration could influence seeing the endpoint, (4) the endpoint is referenced to reading a chart of unspecified brightness and brightness of the reading chart can influence the readability of symbols, and (5) the time interval between light stimulation and physical transfer to a reading chart may be longer than the recovery time.

Prior methods of photo stressing entail flooding the eye with a diffuse light source, which stimulates the retina far beyond the central retina, the macula. It is the macula that is the target for photo-stress testing, which is populated by cones and is the center for reading and color vision. The sole purpose of photo-stress is to evaluate macular function; it is not necessary to stimulate the entire retina. Novel to my invention is focal light stimulation that confines photo-stress to the central part of the retina, the macula. Also novel to my invention is the concept of relative photo-stress where the endpoint is the simultaneous comparison of two regions of brightness. Central macular stimulation and relative brightness endpoints are key elements of my invention for both monocular and binocular photo-stress testing, as I shall disclose.

This invention describes focal macular stimulation for photo-stress testing where the relative brightness sense is compared either binocularly or monocularly. The binocular version utilizes binocular brightness rivalry as described in Hofeldt patent (US 20130100400 A1), which is termed the Hofeldt Bridge® and the monocular version utilizes central macular brightness verses peripheral retina brightness during and after the recovery time. In the Hofeldt patent, rivalry was used to identify diseases that cause loss of brightness in the affected eye due to neuronal dysfunction. I have discovered a new application of the Hofeldt Bridge® using light stimulation to one eye that produces temporary reduction of brightness in that eye as compared to the opposite eye that can last from 15 seconds to 5 minutes or more depending upon the testing parameters. The Hofeldt Bridge® provides precise brightness comparison between the two eyes with an endpoint that is easy to judge, simply the relative brightness comparison of a top visual impression to a bottom visual impression. For the monocular version, focal light stimulation of the central macular produces a dark round central afterimage; using a bull's eye configuration, the endpoint is when the center of the bull's eye representing the light stimulated area becomes equally bright as the peripheral ring of the bull's eye that represents the non-stimulated peripheral retina. The endpoints of both methods are based solely upon relative brightness, totally different than the conventional photo-stress endpoint of identifying or not identifying symbols.

This application will describe four embodiments for measuring photo-stress: (1) a mechanical stereo-viewer for monocular and binocular testing, (2) a graphic display device with a double polarizing filter system for monocular and binocular testing, (3) a graphic display device viewed through a stereo-viewer for monocular and binocular testing, and (4) a graphic display device viewed directly for monocular testing.

DETAILED DESCRIPTION OF THE INVENTION

Detailed descriptions of the embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriate detailed invention, structure or manner. In the drawings, R for right and L for left labels have been included to clarify positions.

The Hofeldt Bridge® consists of at least two rivalrous stimulus pairs aligned vertically where each pair has a bright and a dim stimulus and where the bright stimulus in one pair is viewed by the left eye and in the other pair by the right eye, a reciprocal arrangement. By convention in this application, the left eye views the top impression (left eye stimulus is brighter than right eye stimulus) and the right eye views the bottom impression (right eye stimulus is brighter than the left eye stimulus) as illustrated in FIG. 16. For normal sighted people viewing two vertically aligned reciprocal brightness pairs of identical brightness values, the resulting top and bottom impressions appear of equal brightness. For people with defective vision in one eye causing loss of brightness, the two vertically aligned top and bottom impressions will not appear equally bright; by convention the top impression appears dim when the left eye is defective and the bottom impression appears dim when the right eye is defective.

The testing procedure for rivalrous photo-stress testing using the Hofeldt Bridge® consists of (1) establishing the baseline brightness sense balance of the patient by adjusting the right-left brightness until the fused rivalrous stimulus pairs appear of equal brightness (this step balances the brightness for those with a defect in one eye), (2) using the established baseline, stress the macula of one eye for a specified duration with a bright light stimulus on a black backdrop having an embedded timer displaying seconds in black numbers to signal light ON and light OFF and serving as a fixation point, preferable with a focal beam of a diameter subtending an angle less than that of a 20/400 symbol (the impression seen by the eye that received photo-stress will appear to be relatively darker), (3) measuring with a second embedded timer the duration (recovery time) until the fused stimulus pairs appear of equal brightness, (4) wait a sufficient time (preferably 5 to 10 minutes) for the eyes to fully recover before stressing the opposite eye, (5) stress the macula of the opposite eye using the same parameters, (6) time the duration (recovery time) until the fused stimulus pairs appear of equal brightness, and (7) compare the recovery times to the opposite eye and to a external standard. A macular disease is signally when the recovery time between the two eyes differ significantly from each other or from the standard.

My monocular photo-stress testing consist of (1) providing a black backdrop for focal light stimulation of the eye, (2) stressing the macula of one eye for a specified duration measured with an embedded timer by a bright focal light stimulus of specified brightness of a diameter subtending an angle preferably less than that the dimensions of a 20/400 symbol, (3) observing a "bull's eye" backdrop immediately after photo-stress light for judging the recover time by comparing the photo-stressed white center of the bull's eye to the non-photo-stressed peripheral white ring, (4) measuring the time (with a second embedded timer) for the dark afterimage within the central bull's to appear equally bright as the white peripheral ring (5) stressing the macula of the opposite eye under the same parameters and (6) compare the recovery times to the opposite eye and to a external standard. A macular disease is signally when the recovery time between the two eyes differ significantly from each other or from the standard. Monocular photo-stressing can be performed on a graphic display device within a stereo viewing where each eye is stressed independently while both eyes are open or by observing a graphic display device and closing the eye not being stressed.

I have four embodiments for administrating relative brightness photo-stress testing: (1) a mechanical stereo-viewer for monocular and binocular testing, (2) a graphic display device with a double polarizing filter system for monocular and binocular testing, (3) a graphic display device viewed through a stereo-viewer for monocular and binocular testing, and (4) a graphic display device viewed directly for monocular testing.

My first embodiment is illustrated in the frontal view in FIG. 1 by stereo-viewer 1 constructed of metal or plastic having left chamber 2 and right chamber 3 connected by rectangular bar 11 which is adjustable to accommodate different inter-pupillary distances. Bar 11 is connected to left chamber 2 by bracket 14a having removal baseplate 14b and to right chamber 3 by bracket 15a having a removal baseplate 15b attached by screws. Retainer 12 and 13 limits the excursion of bar 11 and setscrews 16 and 17 secures bar 11, which maintains the spacing between chamber 2 and chamber 3. Cable 10 connects the electronics of chambers 2 and 3. Optical lenses 8 and 9 provide clear focus of test stimuli and wheels 6 and 7 adjust focusing of lenses 8 and 9. Knobs 4 and 5 attach to potentiometers, which adjust the voltage of the illuminating bulbs and thereby the brightness of the test stimuli.

In FIG. 2 is the rear view of stereo-viewer 1 showing the readout of digital voltmeters 20 and 21. The voltage is adjusted by turning the knobs 4 and 5 of potentiometers. In FIG. 3 in a top view of stereo-viewer 1 with the top panel remove to show the interior mechanisms. In FIGS. 4 and 5 are side views, FIG. 4 shows the side panel attached and in FIG. 5 the side panel is removed. Four of screw 41 fit into four of nut 43 to secure the panel. Lens frames 50 and 51 move forwards and backwards to accommodate the focusing needs of the patient. In FIG. 3 frame 50 is supported and slides on smooth rods 32a, 32b and 32c and is propelled by a screw mechanism where by turning threaded wheel 6 that meshes with threaded rod 30 moves frame 50. Referring to FIG. 6, Frame 51 shows opening 53a that receives rod 33a, opening 53b that receives rod 33b, opening 53c that receives rod 33c and threaded rod 31 attaches to nut 55, nut 55 prevents threaded rod 31 from rotating. The same mechanism is deployed for frame 50 where turning wheel 6 moves frame 50 along rods 32a, 32b, and 32c. FIG. 7 is a top view of stereo-viewer 1 showing a window for viewing timer 37 displaying the recovery time.

In FIGS. 9a and 9b are frames 38a and 38b for housing black backdrops 58 and 59. Bull's eye target 52a in backdrop 58 and bull's eye target 52b consists of peripheral ring 97a; black ring 98a and center 99a in backdrop 59 are for monocular photo-stress testing. Bulb 26 (FIGS. 3 and 5) aiming at the center of lens 8 and bulb 27 aiming at the center of lens 9 are the illumination source producing focal light stimulation for photo-stress. The patient is directed to look down at the light during photo-stress. During monocular photo-stress testing of the left eye black backdrop 58 within frame 38a is inserted into stereo-viewer 1 and for right eye testing black backdrop 59 (FIG. 9b) within frame 38b is inserted into stereo-viewer 1. Bulbs 28 and 29, being double or single, provide uniform illumination for comparing the relative brightness of the white center of the bull's eye to the peripheral white ring after photo-stress. Frames 38a, 38b, 39a and 39b slide in and out of stereo-viewer 1, which allows for changing binocular and or monocular stimuli.

For binocular photo-stress stimulation frames 39a and 39b are inserted into stereo-viewer 1. Only bulb 28 and 29 provide background and brightness is individually adjustable with potentiometers. Potentiometer 24 adjusts the brightness of bulb 28 and potentiometer 25 adjusts the brightness of bulb 29 and are powered by battery 36 through Electronic Control Unit (ECU) 35 while the voltage of the circuits are visible on digital voltmeters 20 and 21. The voltage and bulb brightness are linearly related. The patient rotates knob 4 or 5, which changes the voltage of the circuit feeding the bulbs 28 or 29 until the vertically aligned rivalrous stimulus pairs appear equally bright. This sets the baseline or starting point, which must be where the brightness appears equal in the two eyes. In FIGS. 10a and 10b are fusible stimuli consisting of stimulus pair 56a and 56b and stimulus pair 57a and 57b. The patient simultaneously views stimulus pair 56a and 56b and stimulus pair 57a and 57b. Upon binocular fusion, stimuli 56a and 56b fuse to form a single top impression and stimuli 57a and 57b fuse to form a single bottom impression. When the Hofeldt Bridge® is balanced, the resultant top and bottom impressions that are viewed simultaneously will appear of equal brightness, which is an easily recognizable endpoint. For the normal sighted patient the voltage displayed on voltmeters 20 and 21 is the same, but for a patient with a defect, the voltage displayed on voltmeters 20 and 21 are different. When there is a defect in one eye, the fused top and bottom impressions will not appear of equal brightness when the voltmeters are of equal voltage. To bring the two eyes into balance, the potentiometer is adjusted by dimming the bulb brightness to the healthier eye until the top and bottom impressions appear of equal brightness; when the Hofeldt Bridge® is in balance the voltmeter feeding the circuit of the healthier eye will show the lower voltage. The Hofeldt Bridge® must be balanced prior to photo-stress testing because the endpoint of photo-stress testing is when the top and bottom impressions appear equally bright. If the top and bottom impression are unequally bright prior to photo-stress stimulation, the endpoint of equal brightness cannot be obtained. The procedure is to adjust brightness until the endpoint of equality is achieved and at that setting apply focal photo-stress with bulbs 26 or 27, first to one eye and clock the recovery time, and then photo-stress the opposite eye and clock the recovery time.

Turn back to FIG. 7 where top panels are attached. Timer 37 integrated into ECU 35 is visible and displays the time elapsed for recovery from photo-stress stimulation. The remote illustrated in FIG. 8 is wireless and controls the multiple functions of stereo-viewer 1, which are illustrated in the circuit diagram of FIG. 11. Button 71 powers both potentiometer and the patient turns knobs 4 and 5 (FIG. 3) manually to adjusts the brightness for measuring the baseline Hofeldt Bridge® brightness balance status. Button 72 controls the timer, the patient signals the endpoint by pressing button 72, which stops the timer for both monocular photo-stress and rivalous photo-stress testing and records the elapsed time. Buttons 73 and 74 activate photo-stress stimulation for rivalrous photo-stress testing, button 73 is pressed for the right eye and button 74 for the left eye. Button 75 and 76 activate photo-stress stimulation for monocular photo-stress; button 75 is pressed for the right eye and button 76 for the left eye. Alternatively, manual switching could be used to activate the above functions.

Photo-stress testing methods will be elaborated on during the detailed description of the other embodiments since the methodology is similar for all embodiments.

My second embodiment designed for both binocular and monocular photo-stress testing consists of a graphic display device with a double polarizing filter system as shown in FIGS. 12-17. The double polarizing filter system was first described in Hofeldt patent (US 20130100400 A1) for measuring the relative brightness sense for other than photo-stress analysis. In FIG. 12 is graphic display device 60 having stimuli 61 and 62 of equal opacity, horizontal polarizing filter 63 and vertical polarizing filter 64. Filters 63 and 64 can be temporarily or permanently attached to the screen surface. Polarizing glasses 65 have a left polarizing filter matching the orientation of filter 63 that transmits stimulus 61. The left eye cannot see stimulus 62 because the vertical polarizing filter 64 blocks the view of the left filter of glasses 65. Likewise the right eye viewing through the right filter of glasses 65 sees stimulus 62 but not stimulus 61. Even though there is depicted only two stimuli, 61 and 62, the Hofeldt Bridge® of two rivalrous stimulus pairs is operative. The brightness rivalrous stimulus pairs are (1) stimulus 61 (100% brightness) seen with the left eye is rivalrous with the black (0% brightness) polarizing blocking filter 63 seen with the right eye and (2) stimulus 62 (100% brightness) seen with the right eye is rivalrous with the black (0% brightness) polarizing blocking filter 64 seen with the left eye. Impressions 80 and 81 have brightness values of 50%, the mean of the rival pairs (0 and 100% brightness). Of note, by inducing partial light blockage within the polarizing system by tilting the polarizing glasses reveals two rivalrous sets of hearts. With partial blocking, brightness changes are proportionate to the two eyes and the rivalrous stimulus pairs remain reciprocally equal and fulfill Hofeldt Bridge® principles. For the normal sighted patient, mental perception 66a registers stimuli 80 and 81 of equal brightness (50%, mean of 100% and 0%). Should stimuli 80 and 81 appear of unequal brightness, one eye has defective vision. For binocular photo stimulation, the baseline brightness of the top and bottom impressions must appear equally bright. To equalize the brightness of the top and bottom impressions, the brighter image is dimmed by toggling though a presentation program series of graded images of decreasing brightness until the two vertical aligned images appear equally bright to the patient. Typically each series has 6 selections ranging from 0 to 1.5 log units of light attenuation in 0.3 log unit increments. In the first series the top impression progressively dims and in a second series the bottom impression progressively dims. The patient toggles through the two series until a selection is made where the top and bottom impressions appear of equal brightness and this becomes the baseline for photo-stress testing for that patient. Once the defect is quantified, a hyperlink links the patient to the correctly balanced baseline for photo-stress testing. Photo stressing is administered only after the imbalance is balanced, so that everyone starts with a balanced brightness status. Once balanced as illustrated in FIG. 12, photo stressing is the same for everyone. The duration of photo exposure is preferably 30 seconds, but can be of other durations. As illustrated in FIG. 13, the routine is to expose the eye (in this case right eye) to a focal light stimulus as seen in perception 66b for a specified time as timer 67b ticks down, followed by presenting the balanced brightness endpoint as in FIG. 14. For a normal patient the endpoint balance is 50% brightness for each eye as illustrated in FIG. 14. For those with a brightness defect, the brightness value would not the same in both eyes at endpoint. When the recovery phase begins as in FIG. 14, timer 77a and impression timer 77b display zero and will show the elapsed seconds as the endpoint is approached. During recovery the patient sees dimly in the photo-stressed eye as shown by impression 81 (right eye) compared to the unstressed left eye in impression 80 of perception 66c. The endpoint of photo-stress is moment when 80 and 81 impressions appear equally bright as illustrated in FIG. 15, in this example the recovery time is 25 seconds as shown by timer 77b in perception 66d.

Monocular photo stressing is much simpler because there is no need to measure the brightness sense balance since each eye is tested independently. My second embodiment allows monocular testing without covering one eye since the polarizing system separates the vision of the two eyes. In FIGS. 16 and 17 is illustrated the technique for photo stressing the right eye, the process is the same for the left eye. While wearing polarizing glasses 65 the program presents focal light stimulus 62 as time (T) ticks away in timers 77a and 77b for a specified period of time. This is seen in perception 66c as impression 62b at time 77b. The patient is instructed to watch the timer, which insures the patient is focusing directly on the light. In FIG. 17 is the bull's eye target consisting of peripheral white ring 97a, black ring 98a and center 97a. Photo exposure causes the center 99b to appear dimmer to the patient than peripheral ring 97b as depicted in FIG. 17. As recovery progresses, center 99b becomes brighter and at the endpoint, peripheral ring 97b and center 99b will appear of equal brightness and at that moment the number appearing on timer 77a and 77b is the recovery time.

My third embodiment entails a graphic display device viewed through stereo-viewer 78 as shown in FIG. 18-35. For this embodiment stereo-viewer 78 having focusing lenses 89a and 89b attaches to graphic display device 60 for viewing stimuli consisting of rivalrous light heart pairs; top heart pair 56a and 56b and bottom heart pair 57a and 57b. The variety of rival stimuli is endless and should not be considered limited to hearts. The rivalous pairs are stacked vertically with the left stimulus of one pair being brighter than the right stimulus and vice versa for the second stimulus pair where the right stimulus is brighter than the left stimulus as seen in FIG. 16. The brightness of 56a and 57b are equal and the brightness of 57a and 56b are equal, and is termed reciprocal brightness. Embedded timer 77a displays the duration of stimulation and recovery. The "T" appearing in drawings signifies timer of unspecified seconds.

FIG. 19 shows stereo-viewer 78 attached to graphic display device 60 and mental perception 66e as the patient views through stereo-viewer 78 in FIG. 20. Top impression 90 and bottom impression 91 should appear of equal brightness at baseline for a normal patient. Should impressions 90 and 91 not appear equally bright, one eye has defective brightness sense. For judging the relative binocular photo-stress endpoint, the baseline brightness of the top and bottom impressions must appear equally bright prior to photo stressing because this is the reference point for recovery. For the patient with normal brightness sense, the top and bottom impression will appear equally bright when their luminous values are equal. For a patient with defective brightness balance, the luminous values of the top or bottom impression must be adjusted until they appear equally bright to the patient. To equalize the relative brightness of the top and bottom impressions, two series of vertically aligned stimulus pairs are presented to the patient where the brightness of one of the stimuli is varied. The first series dims the top impression and a second series dims the bottom impression. The patient toggles through the two series until a selection is made where the top and bottom impressions appear of equal brightness and this becomes the baseline for photo-stress testing for this patient. The preferred brightness different of stimuli in the series is 0.3 log unit increments, but other values may be used.

FIG. 21 depicts the photo-stress stimulation phase where the left eye is photo stressed by light 67a. Mental perception 66f shows bright light impression 67b and timer impression 68b displaying 20 seconds. The recovery phase is depicted in FIG. 22 where top 90 of the photo stressed left eye appears dimmer than impression 91 of the right eye. When the recovery phase reaches the endpoint, impression 90 and 91 become equally bright as shown in mental perception 66h in FIG. 23.

A more elaborate version of my third embodiment is seen in FIGS. 24-35 where the patient is able to observe a range of binocular imbalances to select a brightness match to the central image 101a for the endpoint of binocular brightness balance. In this embodiment multiple rival pairs are consecutively viewed in a ring configuration (rings 105 and 106) where the designated image pairs for judging the relative brightness endpoint is surrounded by rectangles 93 and 94. For neutralizing left eye defects, the right eye attenuating series 106 dims the right eye in a graded series (100%, 75%, 60%, 50%, 40%, 30%, 25%, and 20%) while series 105 is the fixed density series (25%) of the rival images. In FIG. 24, fixed series 105 is on the left and in FIG. 25; fixed series 105 is on the right side. For neutralizing right eye defects the progressive 106 series is on the right side and the fixed 105 series is on the left side as arranged in FIG. 24. Activating hyperlink 90 causes the series of graded stimuli to rotate clockwise and 91 causes counter-clockwise rotation of that series. In FIGS. 24-35 percentages are used to illustrate brightness, where 100% is the brightest and when an image pair fuses, the brightness of the impression is the mean of the individual image values. In FIGS. 24 and 25 images in positions 100a (25% brightness) and 100b (100% brightness) fuse to form the image in position 100c (63% brightness) and images in positions 101a (100% brightness) and 101b (25% brightness) fuse to form the image in position 101c (63% brightness) and together yield impressions 66i and 66j where images in positions 100c and 101c are of equal brightness. Please note that in FIGS. 24 and 25, rings 105 and 106 are transposed. In FIG. 24, right 106 is in position to neutralize a left eye defect and in FIG. 25; left 106 is in position to neutralize a right eye defect. In this embodiment, the stimulation series is arranged such that the eye being photo stressed is the eye-viewing ring 105, this is a convention that provides that the bottom heart is the one that dims during photo-stress as illustrated in FIGS. 26 and 27. In FIG. 28 the left eye is viewing wheel 105 and the right eye is viewing wheel 106 and together fuse to form perception 66k. In FIG. 29 the left eye is being photo stressed as seen in perception 66l, the eye-viewing wheel 105. In FIG. 30 is illustrated an unbalanced left eye defect noted by dark appearing 101c in perception 66m. In FIG. 31 is illustrated the balancing of that defect, which was achieved by advancing ring 106 from 100% to 75% brightness and confirmed by the equal brightness of 100c and 101c in perception 66n. The balanced illustration in FIG. 31 is ready for photo stressing of that left eye defect. In comparison balancing of a right eye defect is illustrated in FIGS. 32 and 33. In FIG. 32, impression 66o shows an apparent darkening of the 101c compared to 100c even though the true brightness of 100c and 101c are equal (63%). To bring this defect into balance, wheel 106 in FIG. 32 is rotated counter clockwise to 60% which yields 43% fused brightness and equalizes the apparent brightness of 100c and 101c of impression 66p as seen in FIG. 33. This right eye is now in balanced and ready for photo stressing.

FIGS. 34 and 35 illustrate for comparison the method of photo stressing a patient without a defect and a patient without a defect. In FIG. 34 is illustrated the method of photo stressing a patient with no defect. Panoramic perception 110 shows fused rival images 100c and 101c of 63% brightness. Perception 66q shows photo-stress stimulus 68b and perception 66r shows relative dimness of 101c due to photo suppression. In Perception 66s, impressions 100c and 101c appear of equal brightness and the eye has recovered. In FIG. 35 is illustrated the method of photo stressing a patient with a defect. Panoramic perception 111 shows fused rival images 100c of 43% and 101c of 63% brightness, which is the endpoint when 100c and 101c appear equally bright to the patient. Perception 66t shows photo-stress stimulus 68b and perception 66u shows relative dimness of 101c compared to 100c due to photo suppression. In Perception 66v, impressions 100c and 101c appear of equal brightness and the eye has recovered from photo-stress.

My third embodiment of viewing a presentation program in graphic display device within a stereo-viewer also provides for monocular photo-stress testing as illustrated in FIGS. 36 and 38. This is the simplest embodiment and ingeniously measures relative monocular photo-stress recovery macula by comparing photo stressed macula to unstressed retina within the same eye. The comparison is between the recovering macula and unstressed more peripheral retina while using a single device. This is unlike traditional photo-stress testing where recovery is based upon reading acuity and requires physically changing from a photo-stressing device to acuity testing device. To encourage fixation during photo stressing, numerals of digital timer 68a appear within focal light 67a to encourage focusing on the bright stimulus as seen in perception 66w. In FIG. 37 a Bull's eye formed by white center 99b, contiguous peripheral rings 97a and 98a where 98a is dark or black and 97a and 99a are the same brightness. Following photo-stress by focal light 67a, center 99b appears darker than ring 97b, which indicates suppression of the macula. During the recovery phase timer 77 appears below the bull's eye for timing of the endpoint as seen in FIG. 37 in perception 66x. The digital timers are a series of number appearing at regular intervals (preferably every second) recorded in a movie format and embedded within the presentation program. In FIG. 38 center 99b of the Bull's eye is equally bright as ring 97b in perception 66y and signals the endpoint of recovery. By simply touching the screen stops the times and freezes the numerical endpoint.

My fourth embodiment is viewing a presentation on a graphic display device without the use of a stereo viewer. This embodiment requires the patient to cover or close the eye not being tested. As seen in FIG. 39, focal light stimulus 67a produces impression 67b of perception 66z1. In FIG. 40 recovery time is being measured as the center 99b of the bull's eye approaches the same brightness as the peripheral ring 97b of perception 66z2. In FIG. 41 recovery is complete as illustrated by equal brightness of center 99b and peripheral ring 97 in perception 66z3. To test the opposite eye, repeat the process with the other eye closed or covered.

BRIEF DESCRIPTION OF DRAWINGS

FIG. 4. Side view of stereo-viewer with top covers attached

FIG. 5. Side view of stereo-viewer with covers removed

FIG. 20. Graphic display device 60 and perception 66e of fused rival image pairs FIG. 21. Left eye focal light stimulus 67b in perception 66f FIG. 22. Post light stimulus showing suppression of 90, 90 appears darker than 91 in perception 66g FIG. 23. Post recovery phase, 90 and 91 appear equally bright FIG. 24. Image arrangement for left eye photo stimulation FIG. 25. Image arrangement for right eye photo stimulation FIG. 26. Focal light 67 aligned to stimulate wheel 105 viewed by the left eye FIG. 27. Focal light 67 aligned to stimulate wheel 105 viewed by the right eye FIG. 28. The arrangement of FIG. 26 prepared for photo stimulation FIG. 29. Photo stimulation of the right eye, which is viewing wheel 105 of FIG. 28

FIG. 40. Graphic display device 60 with presentation showing bull's eye photo-stress target with 99*b* dimmer than 97*b* in perception 66*z*2

FIG. 41. Graphic display device with perception 66*z*3 showing recovery from photo-stress, center 99*b* and peripheral ring 97*b* appear equally bright.

Figure 1:
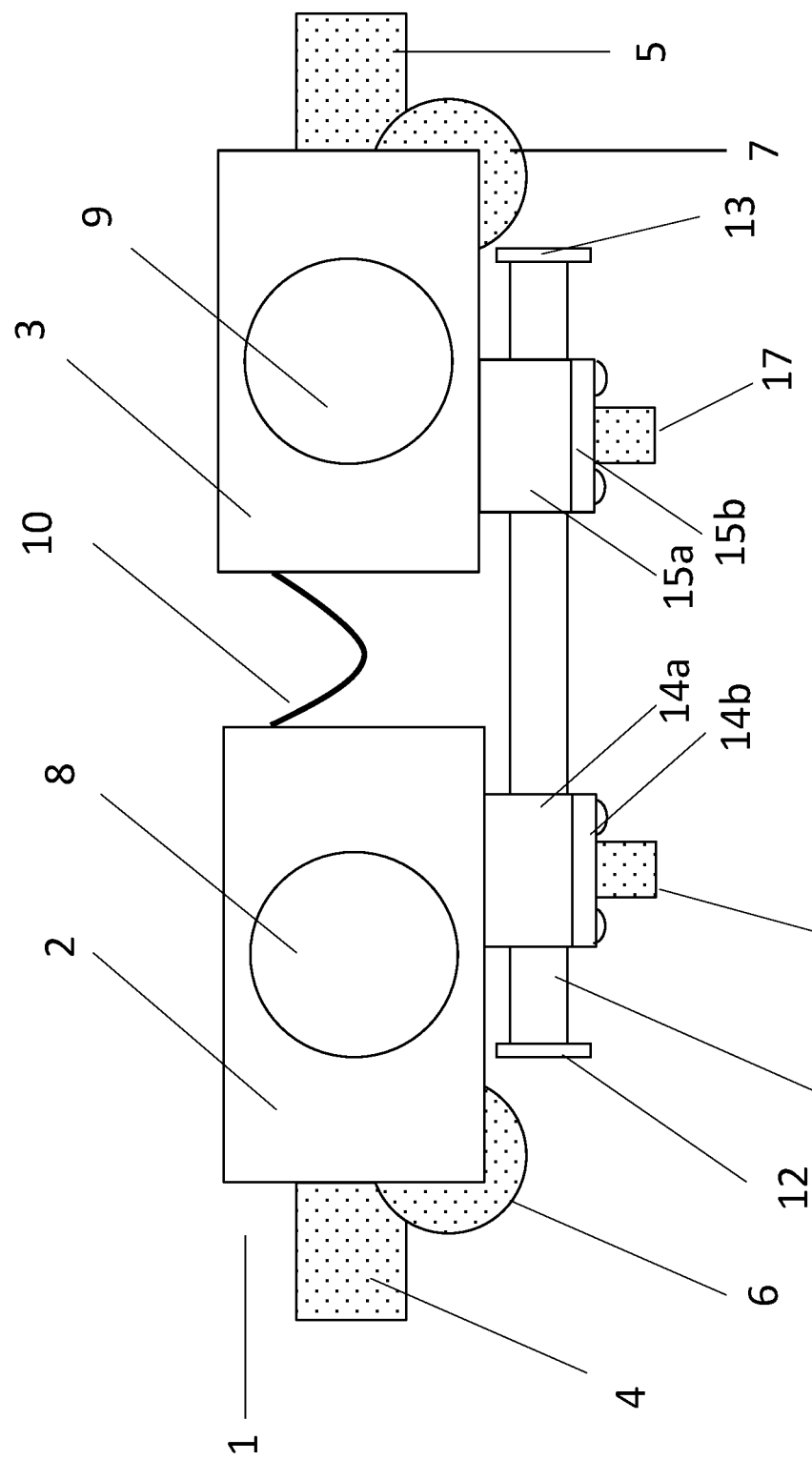
FIG. 1. Frontal view of stereo-viewer
Figure 2:
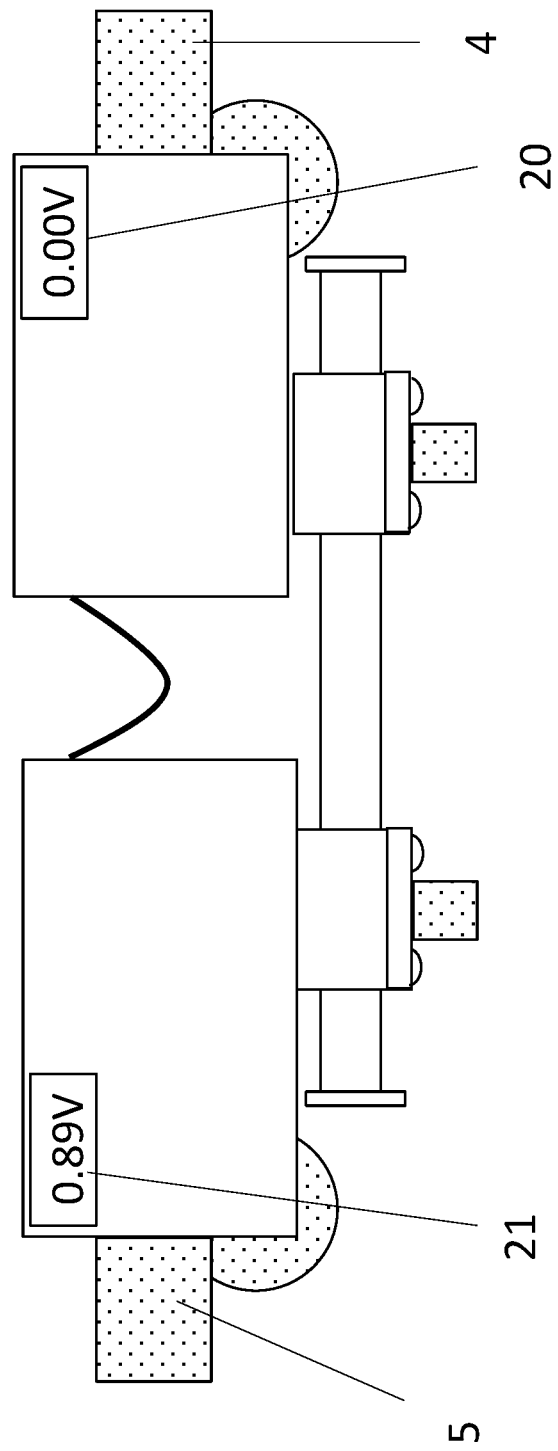
FIG. 2. Rear view of stereo-viewer
Figure 3:
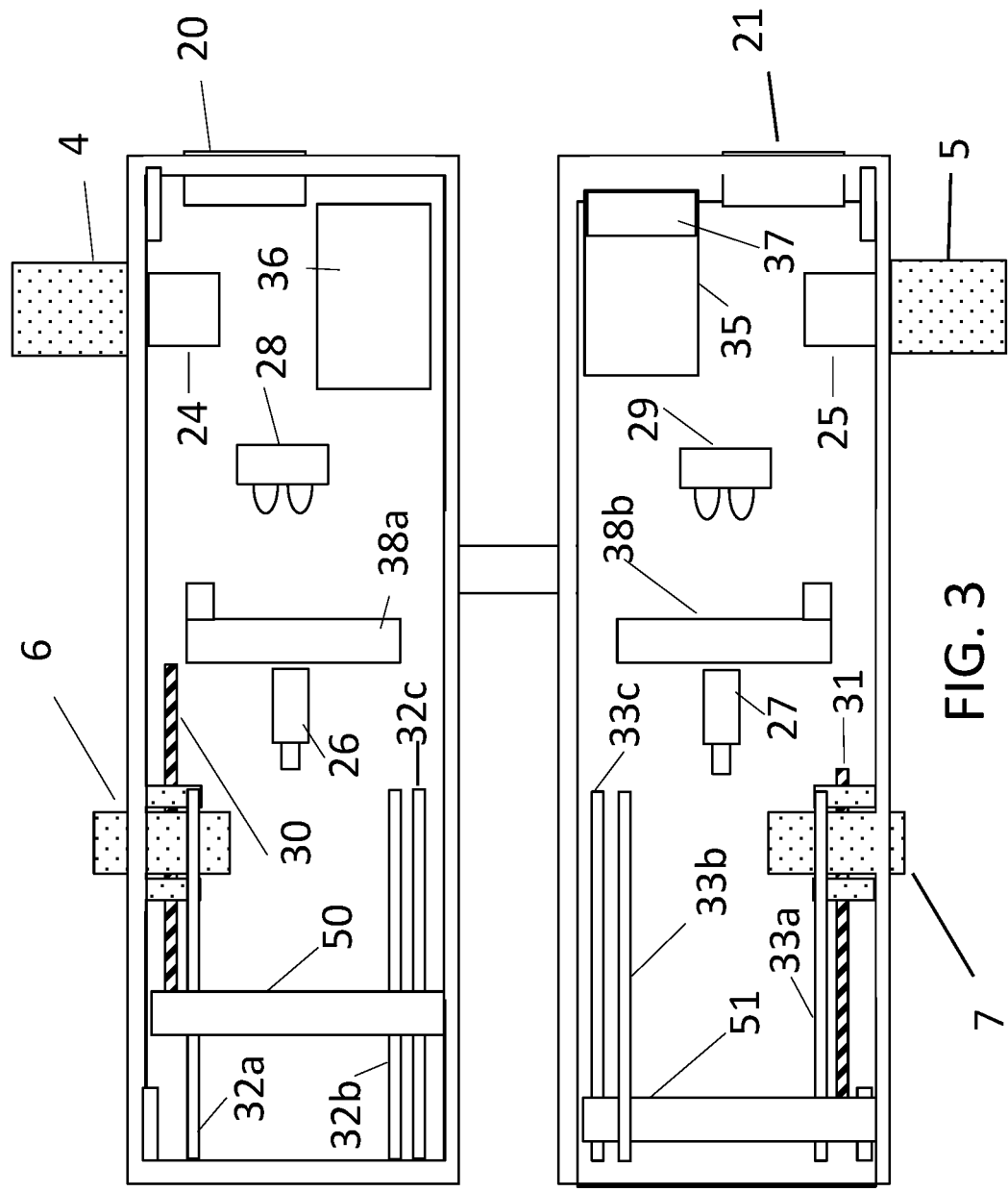
FIG. 3. Top view of stereo-viewer with top covers removed
Figure 6:
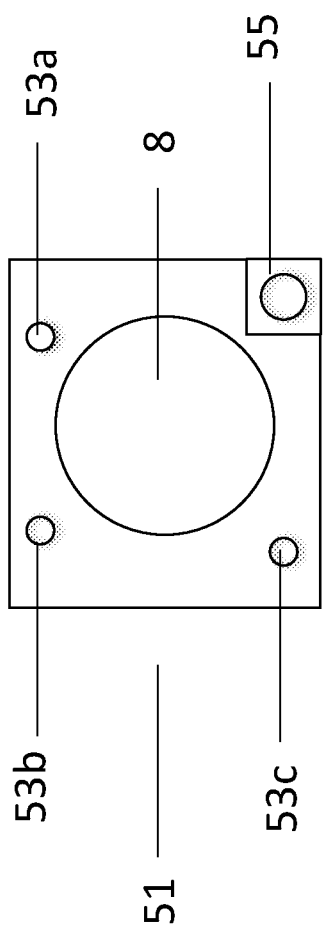
FIG. 6. Fontal view of lens frame
Figure 7:
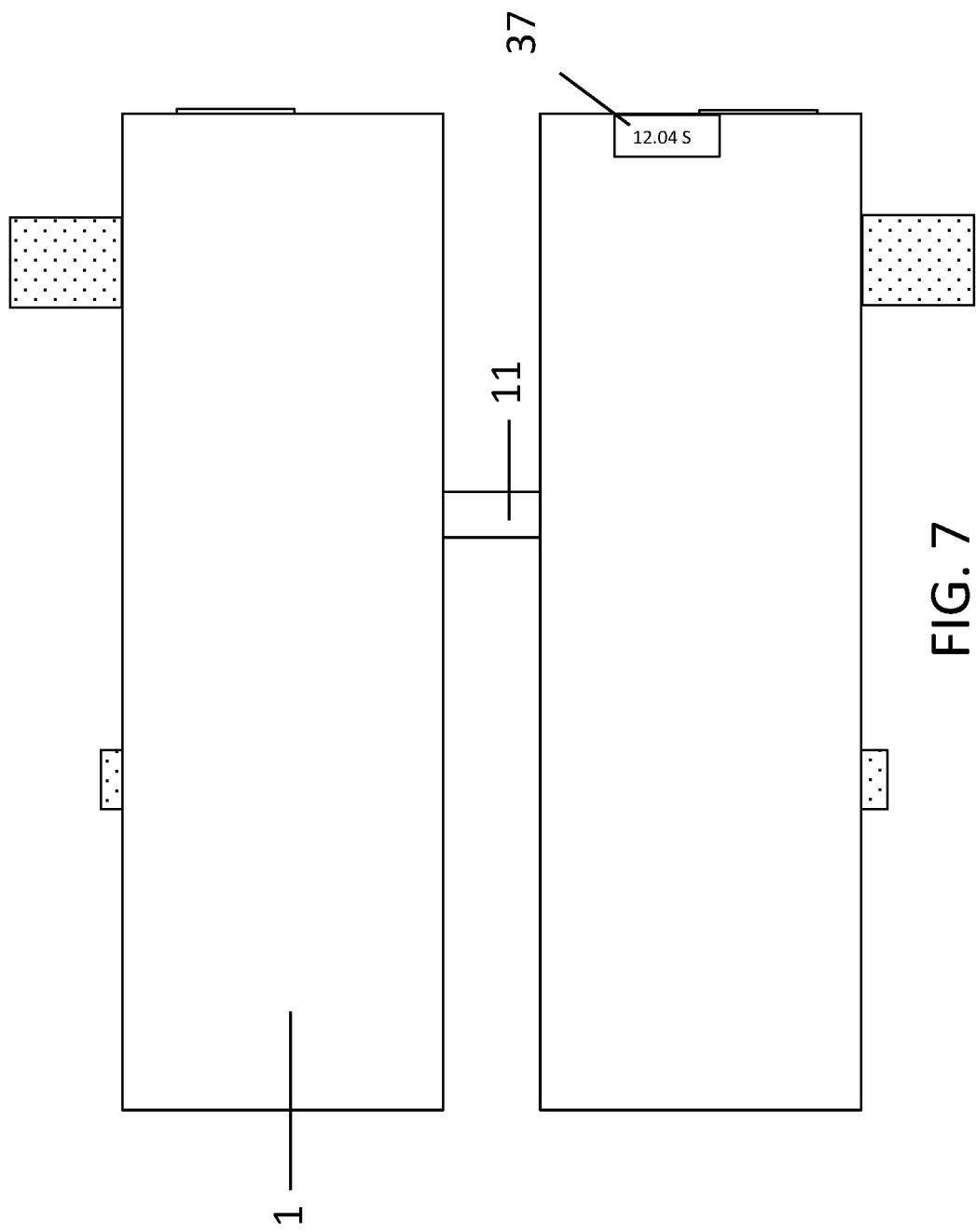
FIG. 7. Top view of stereo-viewer with covers attached
Figure 8:
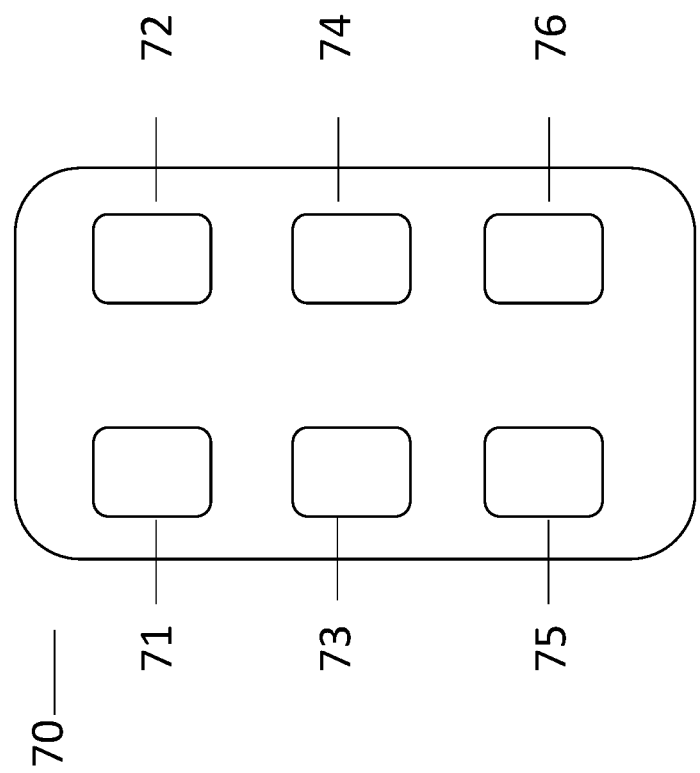
FIG. 8. Top view of wireless remote that communicates with the ECU
Figure 9A:
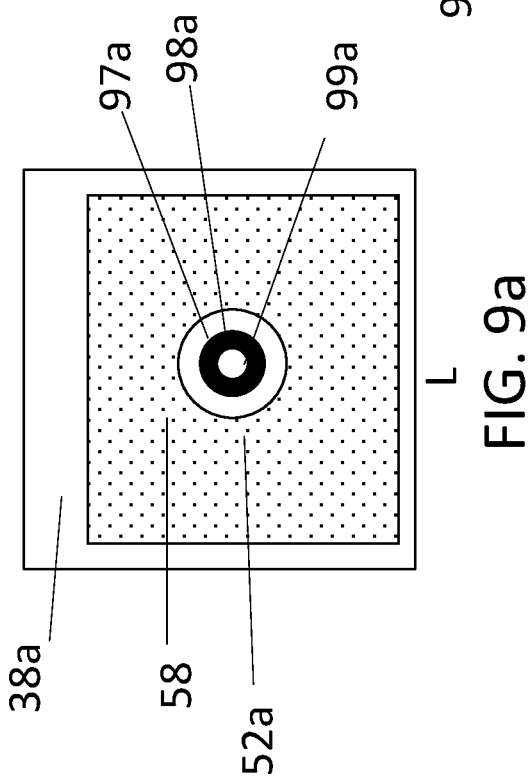
FIGS. 9a and 9b. Front view of frames for housing backdrops
Figure 9B:
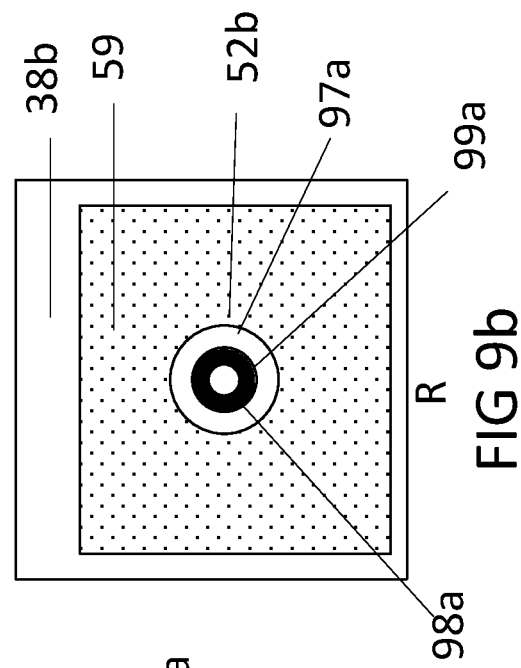
Figure 10A:
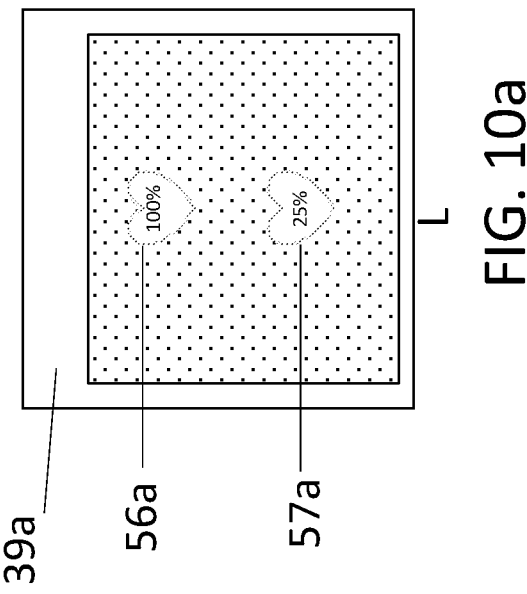
FIGS. 10a and 10b. Fusible stimuli consisting of stimulus pairs
Figure 10:
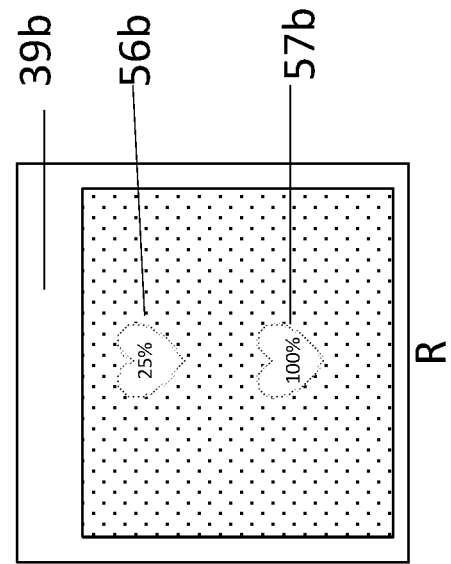
Figure 11:
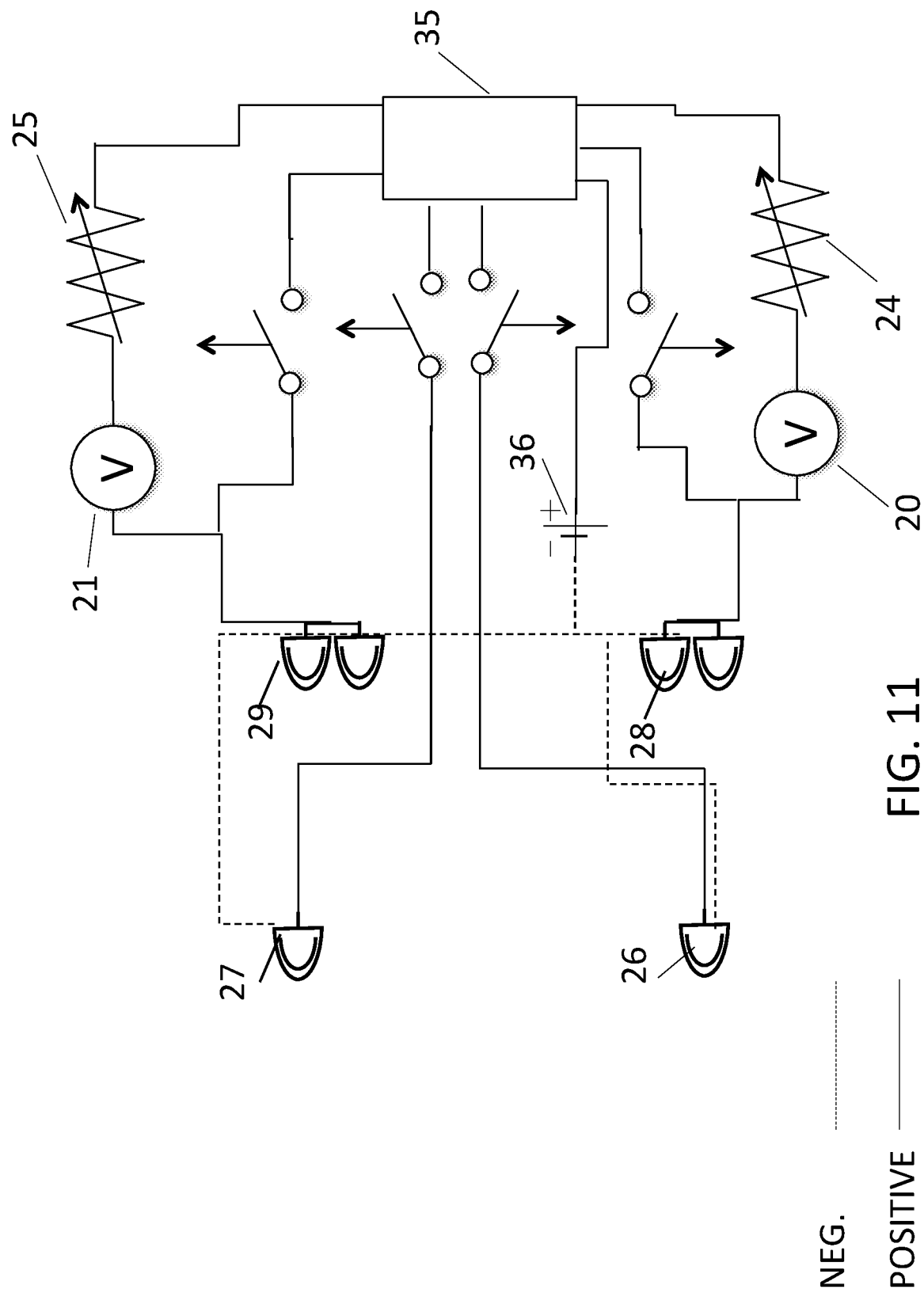
FIG. 11. Circuit diagram
Figure 13:
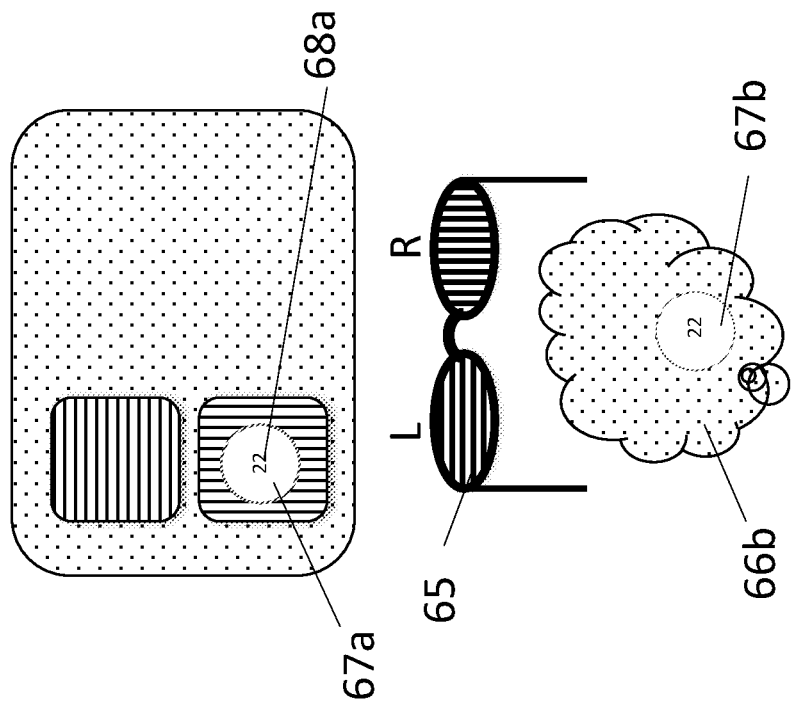
Figure 12:
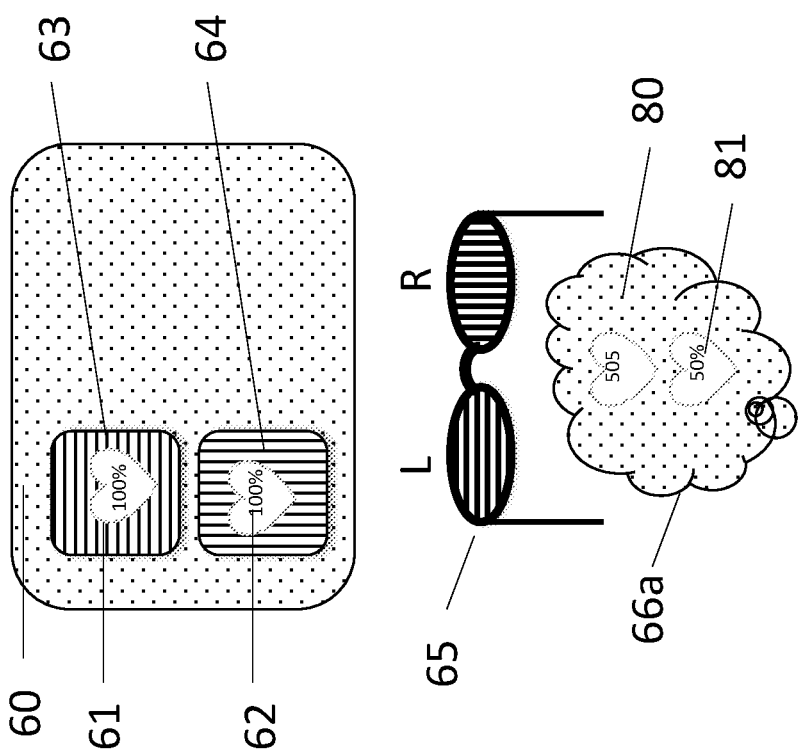
FIG. 12. Graphic display device, double polarizing filter system and stacked stimuli FIG. 13. Graphic display device, double polarizing filter system and focal light stimulus with timer 67b displaying 22 seconds FIG. 14. Beginning of the recovery phase at 0 time, 81 appears darker than 80
Figure 14:
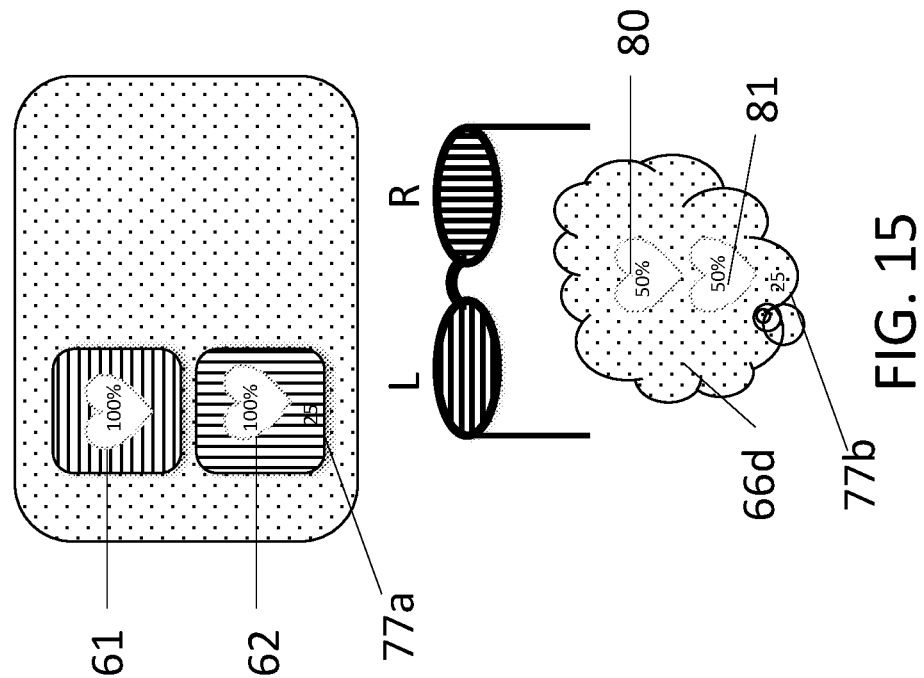
Figure 15:
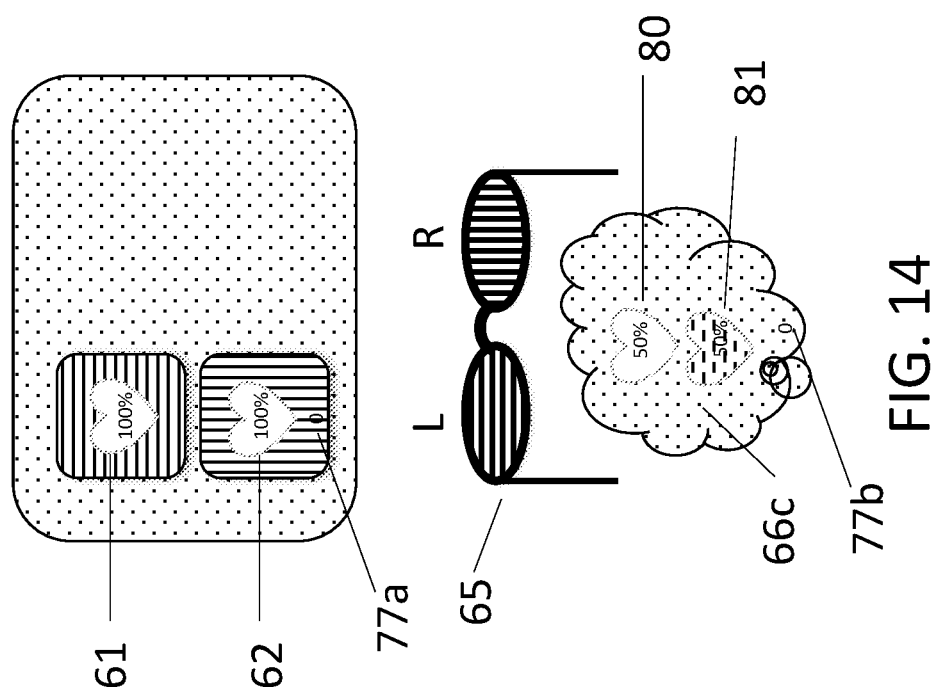
FIG. 15. End of recovery phase (25 seconds), 80 and 81 appear equally bright
Figure 17:
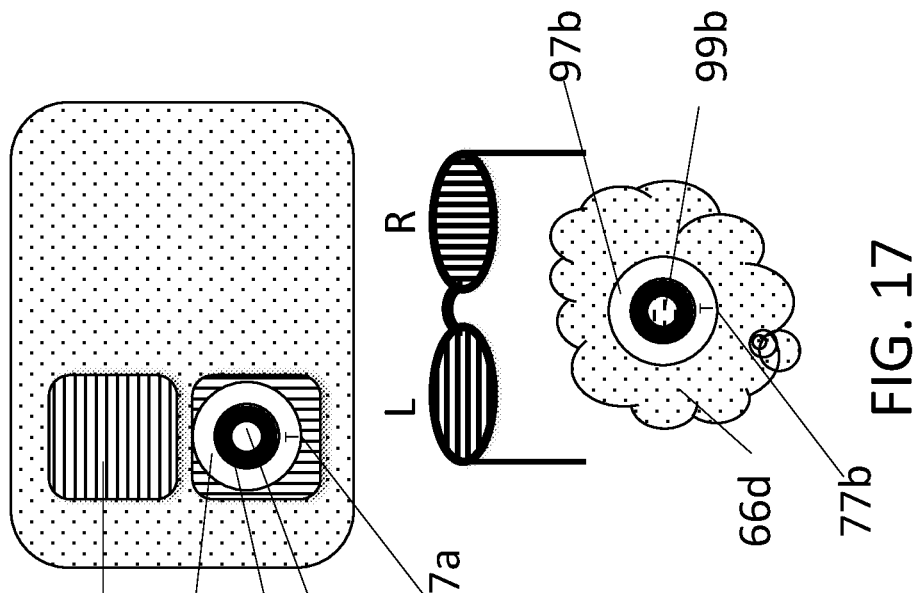
Figure 16:
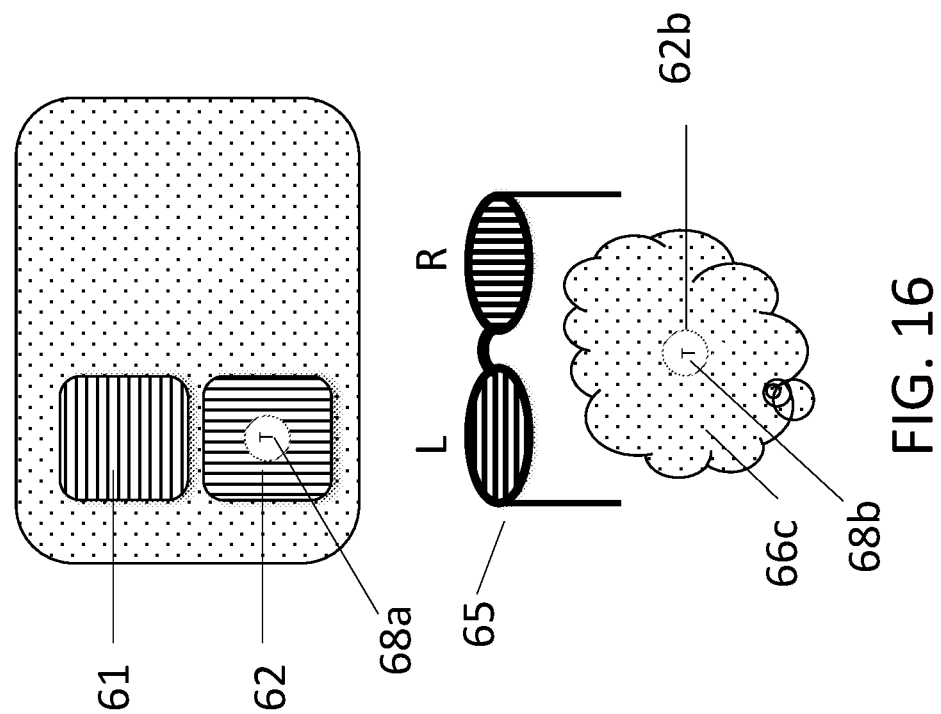
FIG. 16. Graphic display device, double polarizing filter system, and monocular photo stimulation of the right eye FIG. 17. Bull's eye target measuring monocular photo-stress recovery of the right eye FIG. 18. Graphic display device displaying rivalrous stimulus pairs where T signifies timer 77
Figure 19:
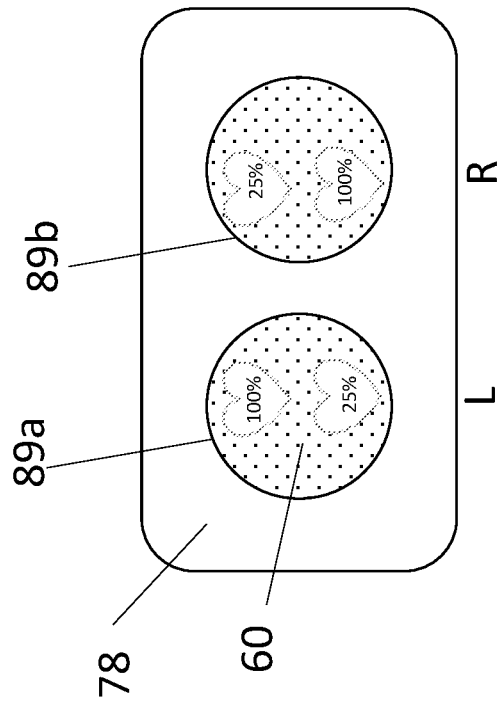
FIG. 19. Stereo-viewer 78 attached to graphic display device 60
Figure 18:
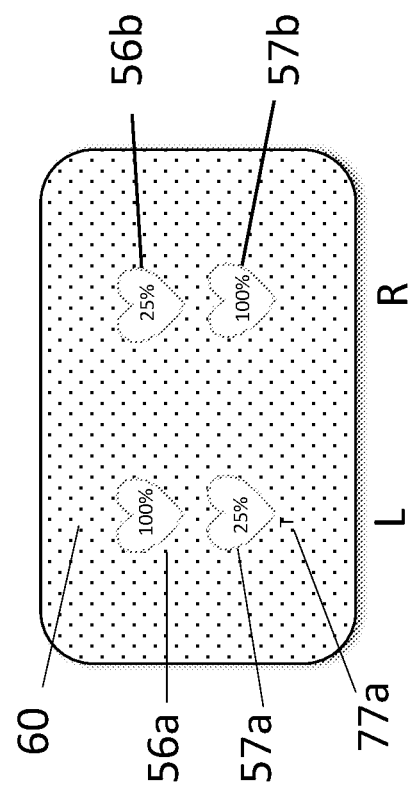
Figure 23:
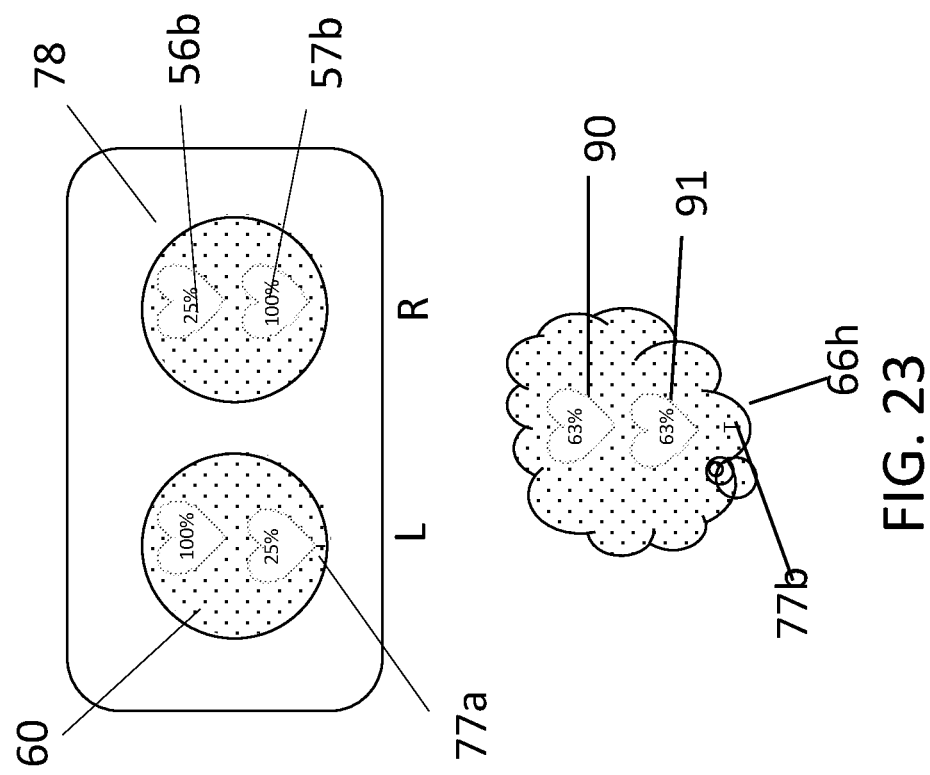
Figure 22:
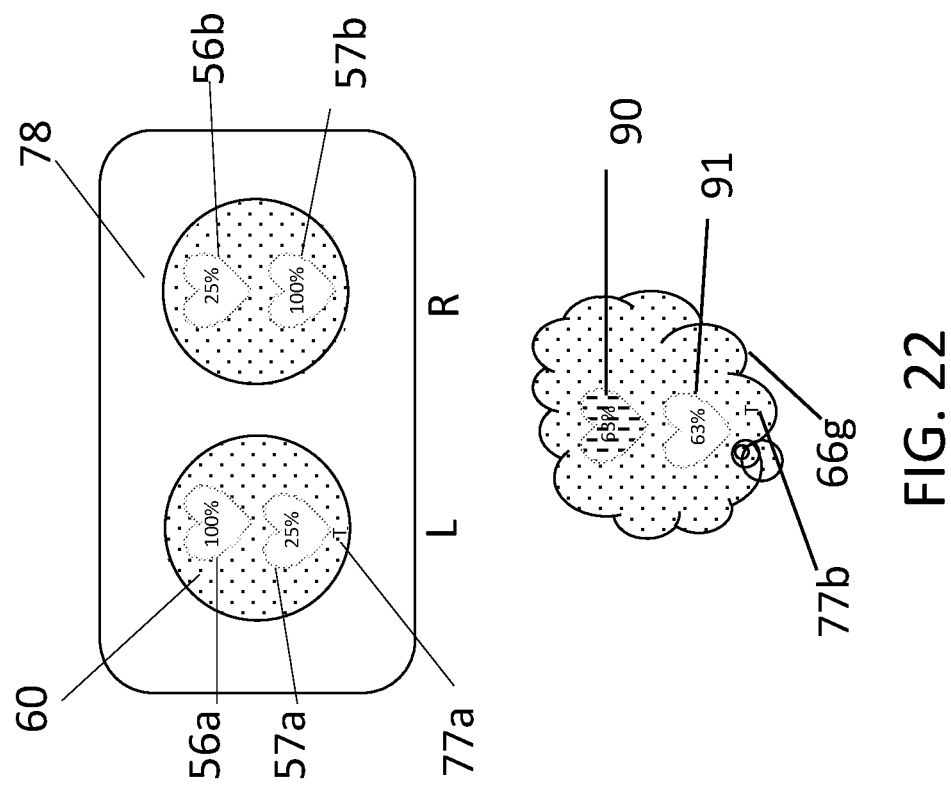
Figure 31:
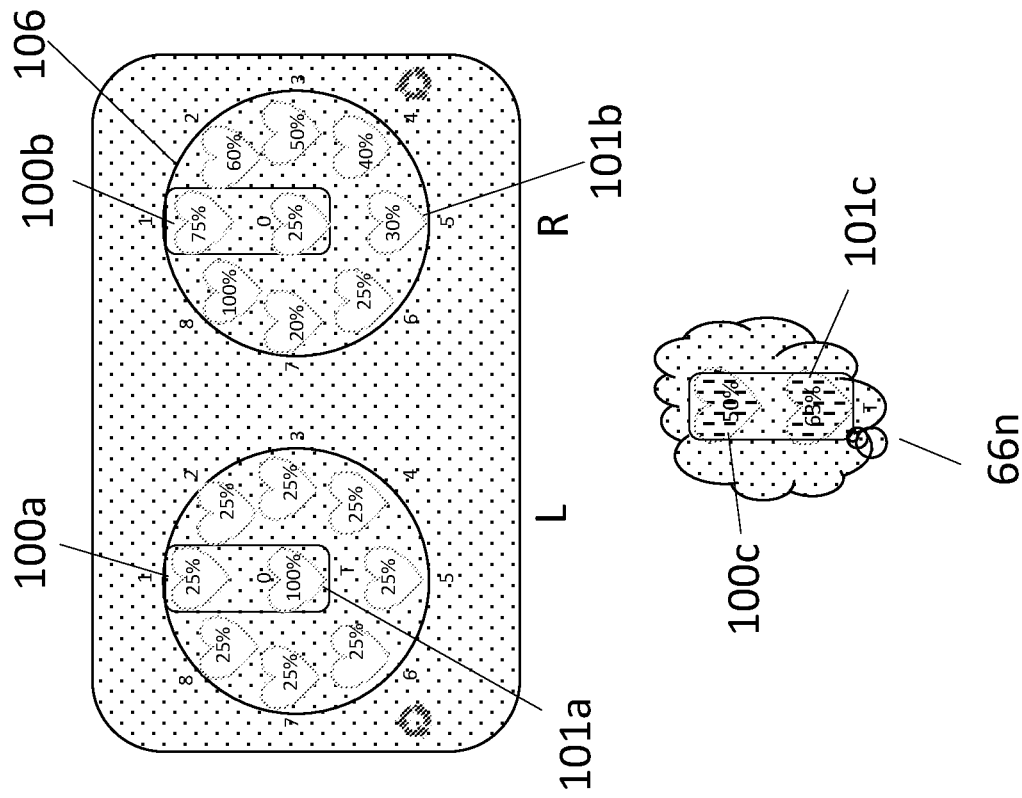
FIG. 31. Recovery of suppression of arrangement of FIGS. 26 and 28, 100c and 101c impressions appear equally bright FIG. 32. Arrangement of a right eye defect, wheel 105 seen by right eye, impression 101c appears darker than 100c FIG. 33. Neutralization of right eye defect, wheel 106 advanced to 60% dimming the left eye, and impressions 100*c* and 101*c* appear equally bright FIG. 34. The sequence of photo stressing an eye without a brightness defect FIG. 35. The sequence of photo stressing an eye with a brightness defect FIG. 36. Graphic display device within a stereo-viewer with presentation showing focal photo stimulation of the left eye FIG. 37. Bull's eye target displayed photo recovery phase from left eye photo stimulation, impression 99*b* appears darker than impression 97*b*
Figure 30:
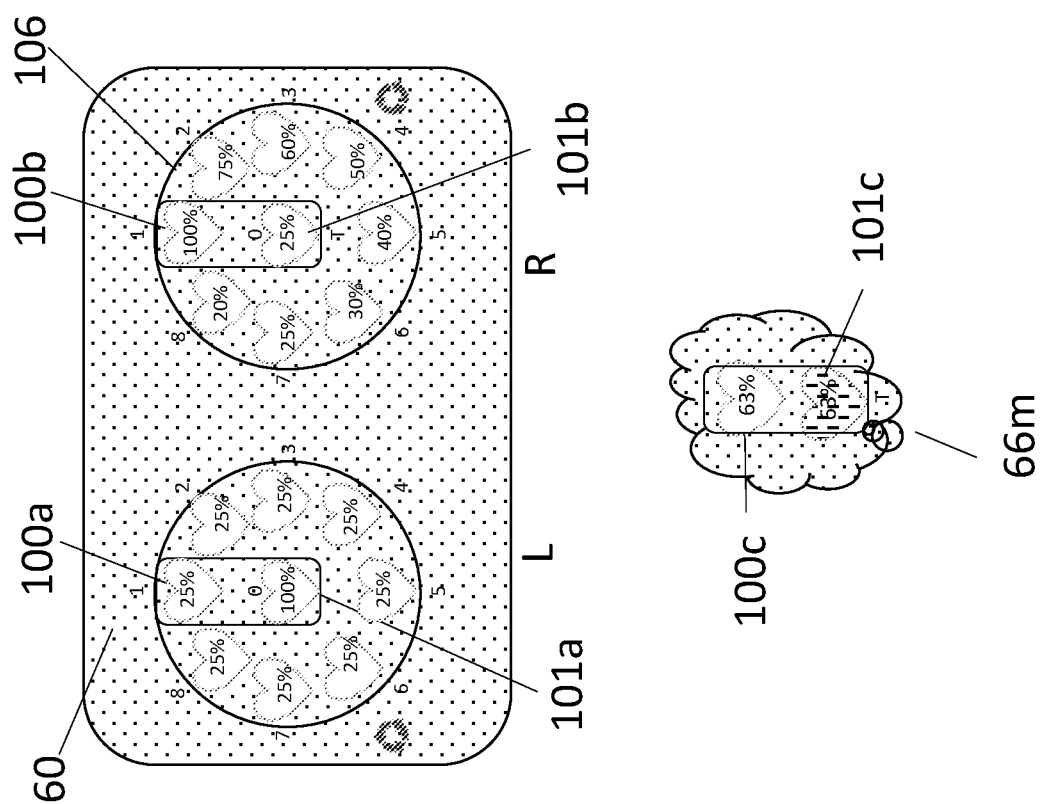
FIG. 30. Suppression of impression 101c of arrangement of FIGS. 26 and 28
Figure 35:
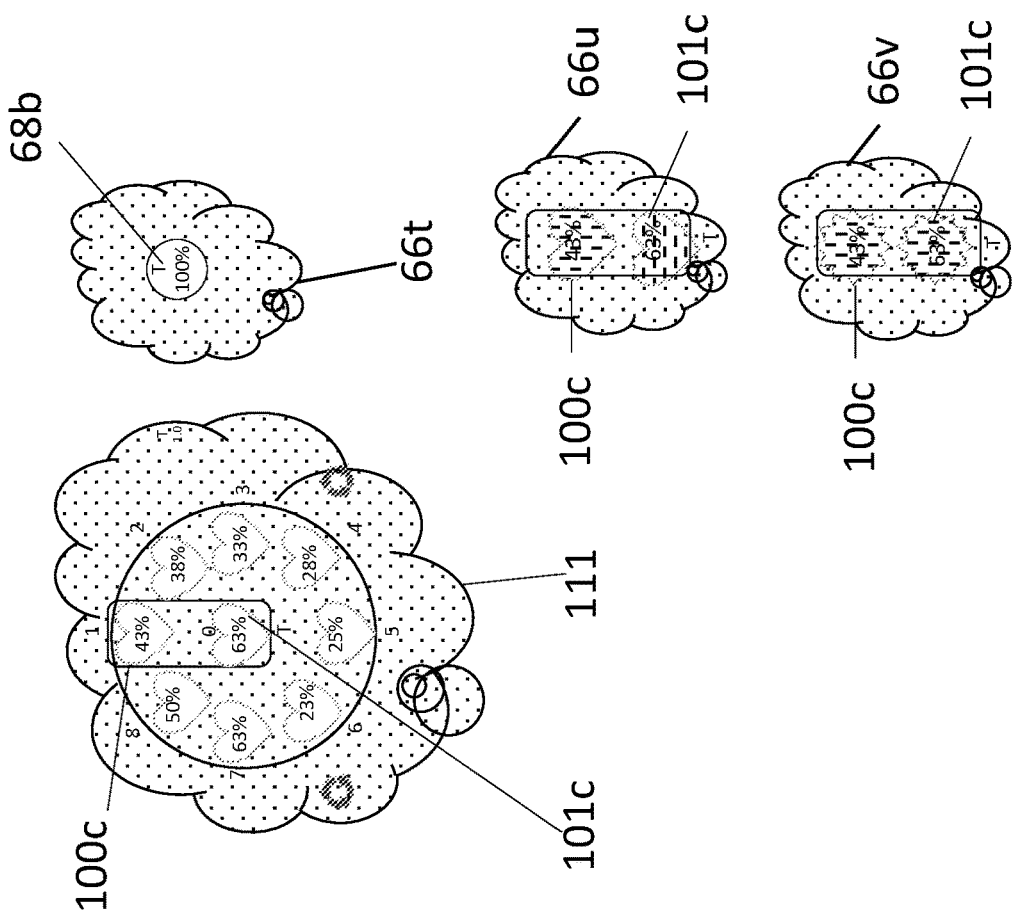
Figure 34:
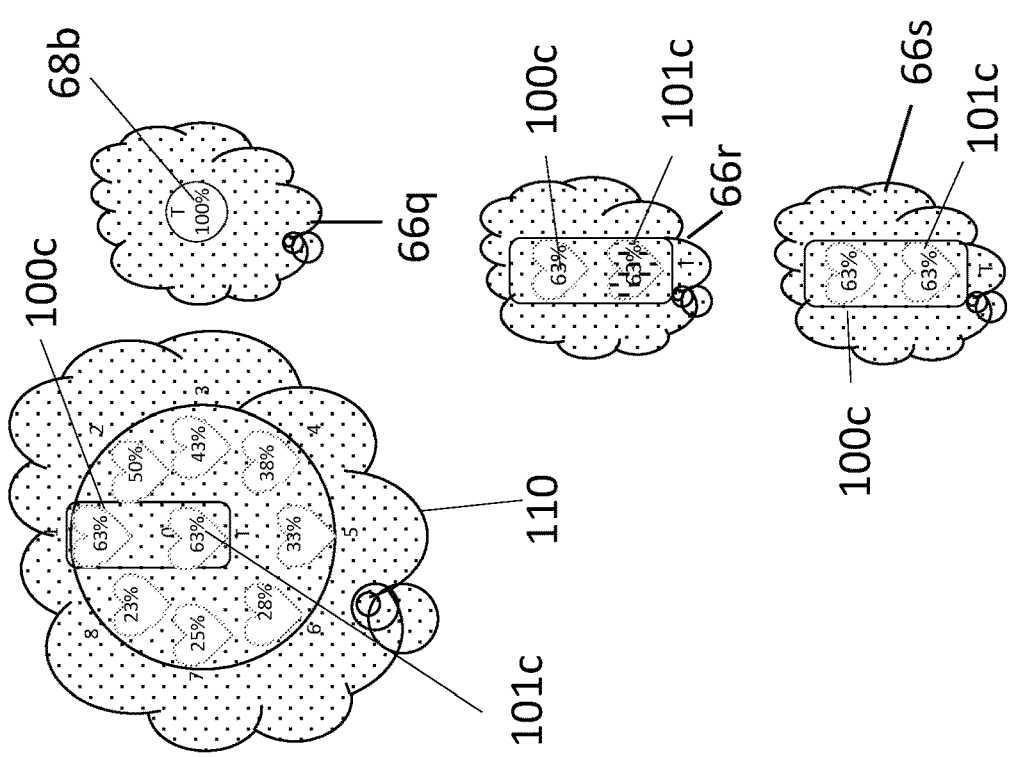
Figure 36:
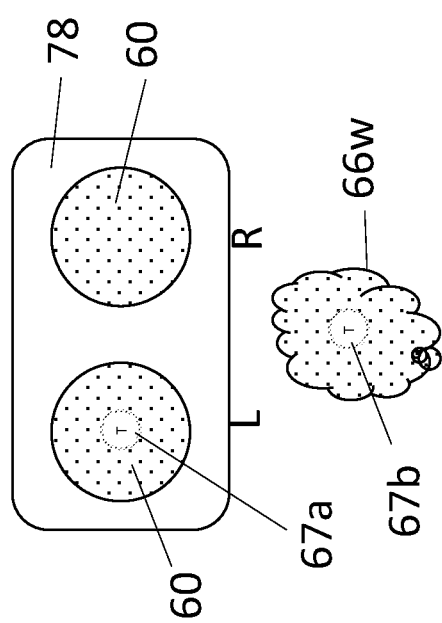
Figure 37:
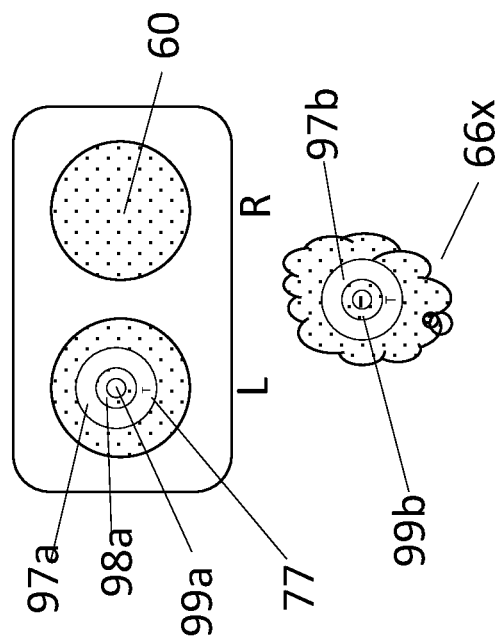
Figure 38:
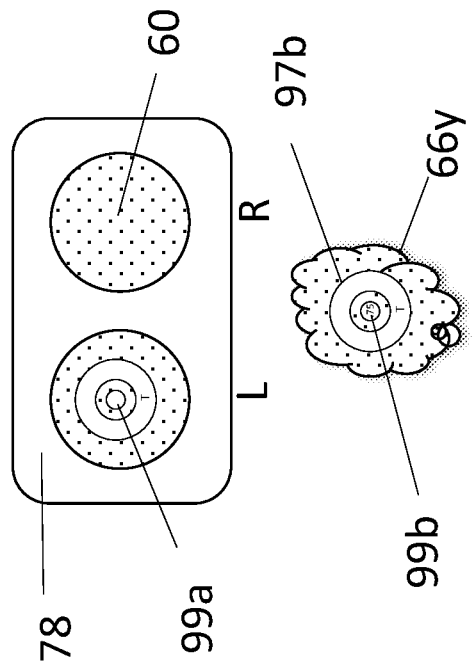
FIG. 38. Bull's eye target showing recovery from left eye photo stimulation, impressions 97*b* and 99*b* appear equally bright FIG. 39. Graphic display device 60 with presentation program showing focal light photo-stress stimulus 67*a*

The invention claimed is:

1. A device for binocular relative photo-stress testing of the macula comprising:
    two pairs of vertically aligned rivalrous light stimulus pairs having a top image pair and a bottom image pair, each pair having a bright stimulus and a dim stimulus, the top image pair and the bottom image pair being configured to fuse to form a top visual impression and a bottom visual impression;
    an adjusting mechanism configured to adjust the brightness of one or both of said rivalrous light stimulus pairs to bring a brightness sense into a balance such that the top visual impression and the bottom visual impression appear equally bright;
    a photo stressing focal light source, the photo stressing focal light source having a focal beam with a diameter subtending an angle of less than that of a symbol with a visual acuity setting at 20/400 configured to photo stress the macula of at least one eye;
    a photo stress recovery endpoint having the bright stimulus of the top visual impression and the bright stimulus of the bottom visual impression having an equal brightness balance; and
    a timer having a digital display configured to display the time that have elapsed, the timer being configured to measure a photo-stress recovery time period where the digital display of the timer is visible.

2. The device of claim 1, further comprising a left chamber and a right chamber, each chamber having one vertically aligned rivalrous light stimulus pair.

3. The device of claim 2, wherein the adjusting mechanism is at least one knob, the at least one knob being secured to a potentiometer, the at least one knob being configured to adjust the brightness of one or both of said rivalrous light stimulus pairs.

4. The device of claim 3, wherein the left chamber has a first voltmeter and the right chamber has a second voltmeter, the at least one knob being configured to adjust a voltage of the first voltmeter and the second voltmeter.

5. The device of claim 4, further comprising a first lens frame and a second lens frame, the first lens frame being disposed within the left chamber and the second lens frame being disposed within the right chamber, the first lens frame and the second lens frame being movable from at least a first position to a second position.

6. The device of claim 5, further comprising a remote control, the remote control being in communication with the potentiometer and configured to control the potentiometer.

7. The device of claim 6, wherein the remote control is in communication with timer, the remote control being further configured to control the timer.

8. A device for monocular relative photo-stress testing comprising:
    at least one frame, the at least one frame having a black backdrop, a bull's eye target with a peripheral outer ring, an inner ring, and a center, the bull's eye target being disposed within the black backdrop;
    at least one photo stressing focal light source, the at least one photo stressing focal light source having a focal beam with a diameter subtending an angle of less than that of a symbol with a visual acuity setting at 20/400 configured to photo stress the macula of at least one eye; and
    a timer having a digital display configured to show the time that has elapsed, the timer being configured to measure a photo-stress recovery period where the digital display of the timer is visible.

9. The device of claim 8, wherein each photo stressing focal light source of the at least one photo stressing focal light source has at least one bulb.

10. The device of claim 8, wherein each photo stressing focal light source of the at least one photo stressing focal light source has two bulbs.

11. The device of claim 8, further comprising a stereo viewer, the at least one frame having a first frame and a second frame, the stereo viewer having a left chamber and a right chamber opposite the left chamber, the first frame being disposed within the left chamber and the second frame being disposed within the right chamber.

12. The device of claim 11, wherein the at least one photo stressing focal light source has a first photo stressing focal light source and a second photo stressing focal light source, the first photo stressing focal light source being disposed within the left chamber and the second photo stressing focal light source from the at least one photo stressing focal light source being disposed within the right chamber.

13. The device of claim 12, wherein the device further comprises a cable and electrical circuitry, the cable being configured to connect the electrical circuitry of the left chamber and the right chamber.

14. The device of claim 13, further comprising a first optical lens and a second optical lens, the first optical lens being disposed within the left chamber and the second optical lens being disposed within the right chamber.

15. The device of claim 8, further comprising a double polarizing system for binocular separation during monocular testing.

16. The device of claim 8, wherein the center of the bull's eye target is white.

17. The device of claim 16, wherein the inner ring of the bull's eye target is darkened and the peripheral outer ring is white.

18. The device of claim 17, further comprising an endpoint of photo stress recovery, the endpoint of photo stress recovery being when the bull's eye target center lightens to equal the white of the peripheral outer ring.

19. The device of claim 18, wherein the peripheral outer ring and the inner ring are contiguous.

20. The device of claim 19, wherein the white of the bull's eye target and the white of the peripheral outer ring are the same.

\* \* \* \* \*